US011274304B2

(12) United States Patent
Kupke et al.

(10) Patent No.: US 11,274,304 B2
(45) Date of Patent: Mar. 15, 2022

(54) PROTECTIVE INTERFERING NUCLEIC ACID MOLECULE AND VIRUS-LIKE PARTICLE, VIRAL VECTOR, OR VIRUS PARTICLE CONTAINING THE SAME AS WELL AS PHARMACEUTICAL COMPOSITION CONTAINING THE PROTECTIVE INTERFERING NUCLEIC ACID AND ITS USE

(71) Applicant: MAX-PLANCK-GESELLSCHAFT ZUR FOERDERUNG DER WISSENSCHAFTEN E. V., Munich (DE)

(72) Inventors: Sascha Kupke, Magdeburg (DE); Timo Frensing, Penzberg (DE); Pawel Zmora, Magdeburg (DE); Udo Reichl, Magdeburg (DE)

(73) Assignee: Max-Planck-Gesellschaft zur Foerderung der Wissenschaften e.V., Muenchin (DE)

( * ) Notice: Subject to any disclaimer, the term of this patent is extended or adjusted under 35 U.S.C. 154(b) by 0 days.

(21) Appl. No.: 16/977,679

(22) PCT Filed: Mar. 5, 2019

(86) PCT No.: PCT/EP2019/055359

§ 371 (c)(1),
(2) Date: Sep. 2, 2020

(87) PCT Pub. No.: WO2019/170625

PCT Pub. Date: Sep. 12, 2019

(65) Prior Publication Data

US 2020/0392504 A1 Dec. 17, 2020

(30) Foreign Application Priority Data

Mar. 5, 2018 (EP) .................................... 18159908

(51) Int. Cl.

| | |
|---|---|
| ***C12N 15/113*** | (2010.01) |
| ***A61K 9/00*** | (2006.01) |
| ***A61K 35/76*** | (2015.01) |
| ***A61K 39/00*** | (2006.01) |

(52) U.S. Cl.

CPC ........ *C12N 15/1131* (2013.01); *A61K 9/0043* (2013.01); *A61K 35/76* (2013.01); *A61K 2039/5258* (2013.01); *C12N 2770/00034* (2013.01)

(58) Field of Classification Search

CPC ...... C12N 15/1131; C12N 2770/00034; C12N 7/00; A61K 9/0043; A61K 35/76; A61K 2039/5258

See application file for complete search history.

(56) References Cited

FOREIGN PATENT DOCUMENTS

| | | |
|---|---|---|
| WO | 2007/135420 A2 | 11/2007 |
| WO | 2017/007839 A1 | 1/2017 |

OTHER PUBLICATIONS

Frensing T, Pflugmacher A, Bachmann M, Peschel B, Reichl U. Impact of defective interfering particles on virus replication and antiviral host response in cell culture-based influenza vaccine production. Appl Microbiol Biotechnol. Nov. 2014;98(21):8999-9008. Epub Aug. 19, 2014. (Year: 2014).*

Cao S, Liu X, Yu M, Li J, JiaX, Bi Y, Sun L, Gao GF, Liu W. A nuclear export signal in the matrix protein of Influenza A virus is required for efficient virus replication. J Virol. May 2012;86(9):4883-91. Epub Feb. 15, 2012. (Year: 2012).*

Database Geneseq (Online); "Influenza A virus sp. matrix gene, Seq ID 7"; XP002781368, Aug. 7, 2008.

Smeenk et al.; "The influenza virus variant A/FM/1/47-MA possesses single amino acid replacements in the hemagglutinin, controlling virulence, and in the matrix protein, controlling virulence as well as growth"; Journal of Virology, vol. 68, No. 1, Jan. 1, 1994, pp. 530-534.

Dimmock et al.; "Cloned Defective Interfering Influenza RNA and a Possible Pan-Specific Treatment of Respiratory Virus Diseases"; Viruses, vol. 7, No. 7, Jul. 8, 2015, pp. 3768-3788.

* cited by examiner

*Primary Examiner* — Rachel B Gill
(74) *Attorney, Agent, or Firm* — WCF IP

(57) ABSTRACT

In a first aspect, the present invention relates to an isolated nucleic acid molecule, in particular, an RNA molecule containing particular substitutions. In a further aspect, the present invention relates to a composition comprising the same as well as virus-like particle, viral vector or virus particle containing the nucleic acid molecule according to the present invention. The virus-like particle, the viral vector or the virus particle is suitable for use as a medicament in particular for treating viral infection. Further, a pharmaceutical composition is provided in particular suitable for use as a pharmaceutical prophylactic vaccine containing the virus-like particle, viral vector or the virus particle or the nucleic acid molecule according to the present invention. Finally, a vaccine for vaccination against viral infection, in particular, influenza viral infection is provided as well as a composition or kit comprising the virus-like particle, viral vector or the virus particle according to the present invention or the nucleic acid molecule according to the present invention in a combination with a wild type viral vector or wild type virus particle said composition or kit is suitable for use in treating or protecting against viral infection.

25 Claims, 3 Drawing Sheets

Specification includes a Sequence Listing.

SEQUENCE LISTING

```
<160> NUMBER OF SEQ ID NOS: 39

<210> SEQ ID NO 1
<211> LENGTH: 1027
<212> TYPE: DNA
<213> ORGANISM: influenza A

<400> SEQUENCE: 1

agcgaaagca ggtagatatt gaaagatgag tcttctaacc gaggtcgaaa cgtacgttct     60

ctctatcatc ccgtcaggcc ccctcaaagc cgagatcgca cagagacttg aagatgtctt    120

tgcagggaag aacaccgatc ttgaggttct catggaatgg ctaaagacaa gaccaatcct    180

gtcacctctg actaagggga ttttaggatt tgtgttcacg ctcaccgtgc ccagtgagcg    240

aggactgcag cgtagacgct ttgtccaaaa tgcccttaat gggaacgggg atccaaataa    300

catggacaaa gcagttaaac tgtataggaa gctcaagagg gagataacat tccatggggc    360

caaagaaatc tcactcagtt attctgctgg tgcacttgcc agttgtatgg gcctcatata    420

caacaggatg gggctgtga ccactgaagt ggcatttggc ctggtatgtg caacctgtga    480

acagattgct gactcccagc atcggtctca taggcaaatg gtgacaacaa ccaacccact    540

aatcagacat gagaacagaa tggttttagc cagcactaca gctaaggcta tggagcaaat    600

ggctggatcg agtgagcaag cagcagaggc catggaggtt gctagtcagg ctaggcaaat    660

ggtgcaagcg atgagaacca ttgggactca tcctagctcc agtgctggtc tgaaaaatga    720

tcttcttgaa aatttgcagg cctatcagaa acgaatgggg gtgcagatgc aacggttcaa    780

gtgatcctct cgctattgcc gcaaatatca ttgggatctt gcacttgata ttgtggattc    840

ttgatcgtct ttttttcaaa tgcatttacc gtcgctttaa atacggactg aaaggagggc    900

cttctacgga aggagtgcca aagtctatga gggaagaata tcgaaaggaa cagcagagtg    960

ctgtggatgc tgacgatggt cattttgtca gcatagagct ggagtaaaaa actaccttgt   1020

ttctact                                                             1027


<210> SEQ ID NO 2
<211> LENGTH: 1027
<212> TYPE: DNA
<213> ORGANISM: influenza A

<400> SEQUENCE: 2

agtaaaaaca ggtagatatt gaaagatgag tcttctaacc gaggtcgaaa cgtacgttct     60

ctctatcatc ccgtcaggcc ccctcaaagc cgagatcgcg cagagacttg aaaatgtctt    120
```

```
tgcagggaag aacaccgatc ttgaggttct catggaatgg ctaaagacaa gaccaatcct    180

gtcacctctg actaagggga ttttaggatt tgtgttcacg ctcaccgtgc ccagtgagca    240

gggactgcag cgtagacgct ttgtccaaaa tgcccttaat gggaacgggg atccaaataa    300

catggacaaa gcagttaaac tgtataggaa gcttaagagg gagataacat tctatggggc    360

taaagaaata gcactcagtt attccgctgg tgcacttgcc tgttgtatgg gcctcatata    420

caacaggatg gggactgtga ctgctgaagt ggtgtttggc ctggtatgtg caacctgtga    480

acagattgct gactcccagc atcggtctca taggcaaatg gtggcaacaa ccaacccact    540

aatcagacat gagaacagaa tggttttagc cagcactaca gctaaggcta tggagcaaat    600

ggctggatcg agtgagcaag cagcagaggc catggaggtt gcgattcggg ctaggcaaat    660

ggtgcaggca atgagaacca ttgggactca tcctagctcc agtgctggtc tgaaagatga    720

tcttcttgaa aatttgcagg cctatcagaa acgaatgggg gtgcagatgc aacggttcaa    780

gtgatcctct cgttattgcc tcaagtatca ttgggatctt gcacttgata ttgtggattc    840

ttgatcgtct tttttcaaa tgcatttacc gtctctttaa atacggtttg aaaagagggc    900

cttctacgga aggagtgcca aagtctatga gggaagaata tcaaaaggaa cagcagagtg    960

ctgtggatgc tgacgatggt cattttgtca gcatagagct ggagtaaaaa actaccttgt   1020

ttctact                                                             1027
```

<210> SEQ ID NO 3
<211> LENGTH: 1027
<212> TYPE: DNA
<213> ORGANISM: influenza A

<400> SEQUENCE: 3

```
agtaaaaaca ggtagatgtt gaaagatgag tcttctaacc gaggtcgaaa cgtacgttct     60

ctctatcatc ccgtcaggcc ccctcaaagc cgagatcgcg cagagacttg aaaatgtctt    120

tgcagggaag aacaccgatc ttgaggttct catggaatgg ctaaagacaa gaccaatcct    180

gtcacctctg actaagggga ttttaggatt tgtgttcacg ctcaccgtgc ccagtgagca    240

gggactgcag cgtagacgct ttgtccaaaa tgcccttaat gggaacgggg atccaaataa    300

catggacaaa gcagttaaac tgtataggaa gcttaagagg gagataacat tctatggggc    360

taaagaaata gcactcagtt attccgctgg tgcacttgcc tgttgtatgg gcctcatata    420

caacaggatg gggactgtga ctgctgaagt ggtgtttggc ctggtatgtg caacctgtga    480

acagattgct gactcccagc atcggtctca taggcaaatg gtggcaacaa ccaatccact    540

aatcagacat gagaacagaa tggttttagc cagcactaca gctaaggcta tggagcaaat    600

ggctggatcg agtgagcaag cagcagaggc catggaggtt gcgattcggg ctaggcaaat    660

ggtgcaggca atgagaacca ttgggactca tcctagctcc agtgctggtc tgaaagatga    720

tcttcttgaa aatttgcagg cctatcagaa acgaatgggg gtgcagatgc aacggttcaa    780

gtgatcctct cgttattgcc tcaagtatca ttgggatctt gcacttgata ttgtggattc    840

ttgatcgtct tttttcaaa tgcatttacc gtctctttaa atacggtttg aaaagagggc    900

cttctacgga aggagtgcca aagtctatga gggaagaata tcaaaaggaa cagcagagtg    960

ctgtggatgc tgacgatggt cattttgtca gcatagagct ggagtaaaaa actaccttgt   1020

ttctact                                                             1027
```

<210> SEQ ID NO 4

-continued

<211> LENGTH: 46
<212> TYPE: DNA
<213> ORGANISM: artificial
<220> FEATURE:
<223> OTHER INFORMATION: probe

<400> SEQUENCE: 4
atttaggtga cactatagaa gcgagtgatt atgagggacg gttgat 46

<210> SEQ ID NO 5
<211> LENGTH: 44
<212> TYPE: DNA
<213> ORGANISM: artificial
<220> FEATURE:
<223> OTHER INFORMATION: probe

<400> SEQUENCE: 5
gctagcttca gctaggcatc agtagaaaca agggtatttt tctt 44

<210> SEQ ID NO 6
<211> LENGTH: 45
<212> TYPE: DNA
<213> ORGANISM: artificial
<220> FEATURE:
<223> OTHER INFORMATION: probe

<400> SEQUENCE: 6
atttaggtga cactatagaa gcgagccgag atcgcacaga gactt 45

<210> SEQ ID NO 7
<211> LENGTH: 44
<212> TYPE: DNA
<213> ORGANISM: artificial
<220> FEATURE:
<223> OTHER INFORMATION: probe

<400> SEQUENCE: 7
gctagcttca gctaggcatc agtagaaaca aggtagtttt ttac 44

<210> SEQ ID NO 8
<211> LENGTH: 42
<212> TYPE: DNA
<213> ORGANISM: artificial
<220> FEATURE:
<223> OTHER INFORMATION: probe

<400> SEQUENCE: 8
atttaggtga cactatagaa gcggatagtg gagcggattc tg 42

<210> SEQ ID NO 9
<211> LENGTH: 44
<212> TYPE: DNA
<213> ORGANISM: artificial
<220> FEATURE:
<223> OTHER INFORMATION: probe

<400> SEQUENCE: 9
gctagcttca gctaggcatc agtagaaaca agggtgtttt ttag 44

<210> SEQ ID NO 10
<211> LENGTH: 33
<212> TYPE: DNA
<213> ORGANISM: artificial
<220> FEATURE:
<223> OTHER INFORMATION: pobe

<400> SEQUENCE: 10
gtaaaacgac ggccagtttt tttttttttt ttt 33

<210> SEQ ID NO 11
<211> LENGTH: 23
<212> TYPE: DNA
<213> ORGANISM: artificial
<220> FEATURE:
<223> OTHER INFORMATION: probe

<400> SEQUENCE: 11
atttaggtga cactatagaa gcg 23

<210> SEQ ID NO 12
<211> LENGTH: 20
<212> TYPE: DNA
<213> ORGANISM: artificial
<220> FEATURE:
<223> OTHER INFORMATION: probe

<400> SEQUENCE: 12
gctagcttca gctaggcatc 20

<210> SEQ ID NO 13
<211> LENGTH: 17
<212> TYPE: DNA
<213> ORGANISM: artificial
<220> FEATURE:
<223> OTHER INFORMATION: probe

<400> SEQUENCE: 13
gtaaaacgac ggccagt 17

<210> SEQ ID NO 14
<211> LENGTH: 18
<212> TYPE: DNA
<213> ORGANISM: artificial
<220> FEATURE:
<223> OTHER INFORMATION: probe

<400> SEQUENCE: 14
cgcactggga tgttcttc 18

<210> SEQ ID NO 15
<211> LENGTH: 22
<212> TYPE: DNA
<213> ORGANISM: artificial
<220> FEATURE:
<223> OTHER INFORMATION: probe

<400> SEQUENCE: 15
ggaaagtgca agaccagaag at 22

<210> SEQ ID NO 16
<211> LENGTH: 24
<212> TYPE: DNA
<213> ORGANISM: artificial
<220> FEATURE:
<223> OTHER INFORMATION: probe

<400> SEQUENCE: 16
tgagcgtgaa cacaaatcct aaaa 24

<210> SEQ ID NO 17
<211> LENGTH: 24
<212> TYPE: DNA

<213> ORGANISM: artificial
<220> FEATURE:
<223> OTHER INFORMATION: probe

<400> SEQUENCE: 17
cattgggatc ttgcacttga catt 24

<210> SEQ ID NO 18
<211> LENGTH: 20
<212> TYPE: DNA
<213> ORGANISM: artificial
<220> FEATURE:
<223> OTHER INFORMATION: probe

<400> SEQUENCE: 18
cactttctgc ttgggtatga 20

<210> SEQ ID NO 19
<211> LENGTH: 21
<212> TYPE: DNA
<213> ORGANISM: artificial
<220> FEATURE:
<223> OTHER INFORMATION: probe

<400> SEQUENCE: 19
ggcgggaaca attaggtcag a 21

<210> SEQ ID NO 20
<211> LENGTH: 12
<212> TYPE: DNA
<213> ORGANISM: artificial
<220> FEATURE:
<223> OTHER INFORMATION: probe

<400> SEQUENCE: 20
agcaaaagca gg 12

<210> SEQ ID NO 21
<211> LENGTH: 20
<212> TYPE: DNA
<213> ORGANISM: artificial
<220> FEATURE:
<223> OTHER INFORMATION: probe

<400> SEQUENCE: 21
aagcaggtag atattgaaag 20

<210> SEQ ID NO 22
<211> LENGTH: 20
<212> TYPE: DNA
<213> ORGANISM: artificial
<220> FEATURE:
<223> OTHER INFORMATION: probe

<400> SEQUENCE: 22
agcgaaagca ggtcaattat 20

<210> SEQ ID NO 23
<211> LENGTH: 25
<212> TYPE: DNA
<213> ORGANISM: artificial
<220> FEATURE:
<223> OTHER INFORMATION: probe

<400> SEQUENCE: 23
agtagaaaca aggtcgtttt taaac 25

<210> SEQ ID NO 24
<211> LENGTH: 20
<212> TYPE: DNA
<213> ORGANISM: artificial
<220> FEATURE:
<223> OTHER INFORMATION: probe

<400> SEQUENCE: 24
agcgaaagca ggcaaaccat 20

<210> SEQ ID NO 25
<211> LENGTH: 25
<212> TYPE: DNA
<213> ORGANISM: artificial
<220> FEATURE:
<223> OTHER INFORMATION: probe

<400> SEQUENCE: 25
agtaggaaca aggcattttt tcatg 25

<210> SEQ ID NO 26
<211> LENGTH: 21
<212> TYPE: DNA
<213> ORGANISM: artificial
<220> FEATURE:
<223> OTHER INFORMATION: probe

<400> SEQUENCE: 26
agcgaaagca ggtactgatc c 21

<210> SEQ ID NO 27
<211> LENGTH: 24
<212> TYPE: DNA
<213> ORGANISM: artificial
<220> FEATURE:
<223> OTHER INFORMATION: probe

<400> SEQUENCE: 27
agtagaaaca aggtactttt ttgg 24

<210> SEQ ID NO 28
<211> LENGTH: 16
<212> TYPE: DNA
<213> ORGANISM: artificial
<220> FEATURE:
<223> OTHER INFORMATION: probe

<400> SEQUENCE: 28
agcaaaagca ggggaa 16

<210> SEQ ID NO 29
<211> LENGTH: 20
<212> TYPE: DNA
<213> ORGANISM: artificial
<220> FEATURE:
<223> OTHER INFORMATION: probe

<400> SEQUENCE: 29
agtagaaaca agggtgtttt 20

<210> SEQ ID NO 30
<211> LENGTH: 22
<212> TYPE: DNA
<213> ORGANISM: artificial
<220> FEATURE:

-continued

<223> OTHER INFORMATION: probe

<400> SEQUENCE: 30
agcaaaagca gggtagataa tc 22

<210> SEQ ID NO 31
<211> LENGTH: 22
<212> TYPE: DNA
<213> ORGANISM: artificial
<220> FEATURE:
<223> OTHER INFORMATION: probe

<400> SEQUENCE: 31
agtagaaaca agggtatttt tc 22

<210> SEQ ID NO 32
<211> LENGTH: 23
<212> TYPE: DNA
<213> ORGANISM: artificial
<220> FEATURE:
<223> OTHER INFORMATION: probe

<400> SEQUENCE: 32
agcgaaagca ggggtttaaa atg 23

<210> SEQ ID NO 33
<211> LENGTH: 25
<212> TYPE: DNA
<213> ORGANISM: artificial
<220> FEATURE:
<223> OTHER INFORMATION: probe

<400> SEQUENCE: 33
agtagaaaca aggagttttt tgaac 25

<210> SEQ ID NO 34
<211> LENGTH: 21
<212> TYPE: DNA
<213> ORGANISM: artificial
<220> FEATURE:
<223> OTHER INFORMATION: probe

<400> SEQUENCE: 34
agcgaaagca ggtagatatt g 21

<210> SEQ ID NO 35
<211> LENGTH: 24
<212> TYPE: DNA
<213> ORGANISM: artificial
<220> FEATURE:
<223> OTHER INFORMATION: probe

<400> SEQUENCE: 35
agtagaaaca aggtagtttt ttac 24

<210> SEQ ID NO 36
<211> LENGTH: 20
<212> TYPE: DNA
<213> ORGANISM: artificial
<220> FEATURE:
<223> OTHER INFORMATION: probe

<400> SEQUENCE: 36
aagcaggtag atattgaaag 20

-continued

```
<210> SEQ ID NO 37
<211> LENGTH: 20
<212> TYPE: DNA
<213> ORGANISM: artificial
<220> FEATURE:
<223> OTHER INFORMATION: probe

<400> SEQUENCE: 37

agtagaaaca aggtagtttt                                              20


<210> SEQ ID NO 38
<211> LENGTH: 20
<212> TYPE: DNA
<213> ORGANISM: artificial
<220> FEATURE:
<223> OTHER INFORMATION: probe

<400> SEQUENCE: 38

agaaaaagca gggtgacaaa                                              20


<210> SEQ ID NO 39
<211> LENGTH: 20
<212> TYPE: DNA
<213> ORGANISM: artificial
<220> FEATURE:
<223> OTHER INFORMATION: probe

<400> SEQUENCE: 39

agtagaaaca agggtgtttt                                              20
```

PROTECTIVE INTERFERING NUCLEIC ACID MOLECULE AND VIRUS-LIKE PARTICLE, VIRAL VECTOR, OR VIRUS PARTICLE CONTAINING THE SAME AS WELL AS PHARMACEUTICAL COMPOSITION CONTAINING THE PROTECTIVE INTERFERING NUCLEIC ACID AND ITS USE

In a first aspect, the present invention relates to an isolated nucleic acid molecule, in particular, an RNA molecule containing particular substitutions. In a further aspect, the present invention relates to a composition comprising the same as well as virus-like particle, viral vector or virus particle containing the nucleic acid molecule according to the present invention. The virus-like particle, the viral vector or the virus particle is suitable for use as an antiviral agent for treating viral infection. Further, a pharmaceutical composition is provided in particular suitable for use as a pharmaceutical prophylactic vaccine containing the virus-like particle, viral vector or the virus particle or the nucleic acid molecule according to the present invention. Finally, a vaccine for vaccination against viral infection, in particular, influenza viral infection is provided as well as a composition or kit comprising the virus-like particle, viral vector or the virus particle according to the present invention or the nucleic acid molecule according to the present invention in a combination with a wild type viral vector or wild type virus particle said composition or kit is suitable for use in treating or protecting against viral infection.

PRIOR ART

The Orthomyxoviridae are a family of RNA viruses which infect vertebrates. Inter alia, influenza virus are a member of this family. Influenza is a viral infection of the respiratory system characterized by fever, cough, and severe muscle aches. Three genera of influenza virus exist, namely, influenza virus A, influenza virus B and influenza virus C which are differentiated by antigenic differences in their nucleoprotein and matrix protein. Viral influenza A and influenza B have eight segments of single stranded, negative-sense RNA, influenza C virus contains seven segments of single stranded RNA (ssRNA).

The major causative agent of human influenza is the type A virus. The virus genome consists of negative sense, single stranded RNA (ssRNA) segments encoding nine structural and two non-structural proteins. Inter alia, segment 7 encodes two matrix proteins, namely, M1 and M2. These two matrix proteins are with overlapping coding sequences.

Human influenza viruses A and B are both responsible for seasonal disease in people, but only influenza A viruses cause worldwide pandemics. In human viruses, various distinct haemagglutinins, i.e. H1, H2 and H3 and several distinct neuraminidases, i.e. N1 and N2, have been identified. These are used for classification of the viruses. There is a continuous shift called antigenic shift in the proteins, thus, allowing escape from the human immune system.

Although an influenza infection elicits a strong immune response against the strain that caused it, the speed with which new strains by antigenic shift leaves a previously infected individual makes the individual susceptible to a new infection. Influenza vaccines have been available commercially for many years including killed and live vaccines as well as recombinant virus-like particles and viral particles. While some vaccines contain inactivated virus particles, more usually the purified HA and NA components are present. Typically, the design of the influenza vaccines is based on the major influenza virus strains causing infection in the previous season. However, because of the phenomenon of antigenic drift, the influenza strains used as the basis of existing vaccines are reassessed from year to year by the WHO and may have to be changed. However, there is always a time lack between the actual infective influenza strain and the components of the vaccines.

Other lines of defense against influenza include antiviral drugs. Various mechanisms are known where these antiviral drugs act on. For example, Amantadine and Rimantadine inhibit the action of a matrix protein, thus, inhibiting the viral RNA to go into the cytosol. Further, Zanamivir and Oseltamivir also known as Relenza® and Tamiflu® are used as antiviral drugs. These drugs block neuraminidase, thus, inhibiting the release of progeny virions from infected cells and the spread of infection.

However, also virus resistant to these antiviral drugs are more and more often found in patient with influenza.

The presence of defective interfering virus, also called DI virus are known since the 1940s. A defective interfering virus disrupts the normal replication and infection cycle of a non-defective virus. Typically, a population of viruses contains a mixture of said defective interfering virus particles as well as normal virus particles. The defective virus particles occur due to spontaneous mutations in RNA segments, e.g. resulting in internal deletions. The DI virus is a non-infectious virus and replicates only when its genome is present in a cell which has been infected by a virus with a complete genome. DI virus has the ability to interfere intracellularly with infectious virus so that it is specifically able to inhibit multiplication of infectious virus. In the following, the DI virus are also referred to as defective interfering particles (DIPs).

DIPs are of viral origin and share the same structural features as their homologous standard viruses (STVs), yet, they typically contain a deleted form of the viral genome (Huang and Baltimore, 1970, Defective viral particles and viral disease processes. Nature 226, 325-328). As a result of the missing genomic information, DIPs are defective in virus replication and can, hence, not result in the production of progeny virions, once infecting a cell. However, upon complementation by the co-infection with fully infectious STV, interference with the normal viral life cycle can be observed with a suppressed STV replication and the release of mainly non-infectious DIPs. This infection outcome is a result of the growth advantage of the defective interfering (DI) genome over the full-length (FL) counterpart, which is manifested by an enhanced genomic replication, the out-competition for cellular or viral resources and a preferential packaging into virus particles (Marriott and Dimmock, 2010). Interestingly, considering the ability of DIPs to suppress virus replication, a growing interest into clinical application of DIPs, for their use as antivirals, can be currently perceived (Dimmock and Easton, 2015, see below).

DIPs were observed for most DNA and RNA viruses, including viruses containing single- and double-stranded genomes. The internal genomic deletions are suggested to arise by an erroneous translocation of the viral polymerase during genomic replication, often referred to as "copy-choice" mechanism. Other DI genomes include multiple-deleted forms, "copyback" or "hairpin" genomes (some parts are repeated in reverse complement form) and "mosaic" genomes (multiple non-adjacent sections are joined together). The precise mechanisms of interference are yet not fully understood. However, it was suggested that DI genomes compete for helper-virus-encoded gene products, in particular for viral polymerases. Furthermore, for influenza A viruses (IAVs), a preferential synthesis of the DI genome over the FL counterpart was observed. In this context, it was proposed that DI genomes show a faster accumulation, due to their reduced length. Moreover, DI genomes of IAVs competitively inhibited packaging of, specifically, their FL parental genomic viral RNA (vRNA), and were further preferentially incorporated into progeny virions.

So far, DI genomes were primarily identified based on their genomic deletion and only little attention was paid to potential nucleotide substitutions.

DI virus is thus also in the focus of developing vaccine against the infectious virus. For example, EP2019685 A describe defective interfering virus being a cloned human DI influenza A virus having a specific RNA segment 1 sequence. Further cloned defective interfering influenza RNA and its use as a possible pan-specific treatment of respiratory virus disease is described by Dimmock M. J. and Easton A. J., Viruses 2015, 7, 3768-3788. The influenza A derived DI genome described therein should allegedly allow to protect by two different mechanisms. Firstly, a molecular interference with influenza A replication and, secondly, by stimulating innate immunity acting against non-influenza A virus. Typically, the DI virus containing defective and interfering influenza RNA of segment 1, segment 2, or segment 3 encoding polymerase proteins.

SUMMARY OF THE PRESENT INVENTION

Treatment with antiviral drugs is limited since treatment has to be started soon after infection. In addition, resistance to antiviral drugs arises rapidly. Further, vaccines comprising virus particles, virus-like particles, viral vectors or on single components, in particular, HA and NA components, are typically based on the annual predictions from the WHO (strains that are most likely to spread and cause illness among people during the upcoming flu season). The DI (DIPs) virus described in the art have not been shown to be successful in influenza vaccination. Thus, new measures to combat viral infection, in particular, influenza A, are urgently needed.

In a first aspect, the present invention provides an isolated nucleic acid molecule comprising a) SEQ ID No. 2 containing the following substitutions of C3T, G4A, G8A, A100G, G113A, G130A, G240A, A241G, C334T, C353T, C361T, C370A, T371G, T385C, A401T, G434A, C442T, A443G, C453T, A454G, A524G, T643G, G645T, A648G, A667G, G670A, A716G, C793T, G801T, A805G, G874T, A887T, C888T, G894A, G943A, compared to the wild type sequence of SEQ ID No. 1;
b) a nucleotide sequence having greater than 98% identity within the sequence of SEQ ID No. 2;
c) a nucleotide sequence that hybridizes with the nucleotide sequence of a) or b) under stringent conditions;
d) a nucleotide sequence complementary to any of the sequences a), b) or c); or
e) mRNA derived from any one of the sequences a), b), c) or d).

In an embodiment, the isolated nucleic acid sequence is a sequence having SEQ ID No. 2 or SEQ ID No. 3 or a functional fragment thereof, In a further aspect, a composition comprising the isolated nucleic acid molecule according to the present invention is provided. Further, a vector or plasmid comprising the nucleic acid molecule according to the present invention is disclosed.

In another aspect, a virus-like particle, a viral vector or a virus particle containing the nucleic acid molecule according to the present invention is disclosed which is particularly a virus-like particle or viral vector derived from an influenza virus, like influenza A virus, or a virus particle from influenza virus, like influenza A virus.

This virus-like particle, the viral vector or the virus particle are useful as a medicament for example in the treatment of a viral infection.

Further host cells containing a nucleic acid vector or plasmid according to the present invention or the nucleic acid molecule according to the present invention is described.

Moreover, pharmaceutical compositions in particular useful as therapeutic or prophylactic vaccines are identified.

In a further aspect, a vaccine for vaccination against viral infection is disclosed. Finally, a composition or a kit comprising a virus-like particle, a viral vector or a virus particle according to the present invention or a nucleic acid molecule according to the present invention, a composition according to the present invention or a vector or plasmid according to the present invention or a host cell according to the present invention in combination with a wild type viral vector or a wild type virus particle, in particular, an influenza viral vector or an influenza virus particle, like influenza A viral vector or influenza A virus particle, e.g. for use in treating or protecting against viral infection is disclosed.

The present invention is based on identifying a so called protective interfering RNA (piRNA) which is characterized in a phenotype different to the phenotype of wild type virus as described below.

DETAILED DESCRIPTION OF THE PRESENT INVENTION

Figure 1:
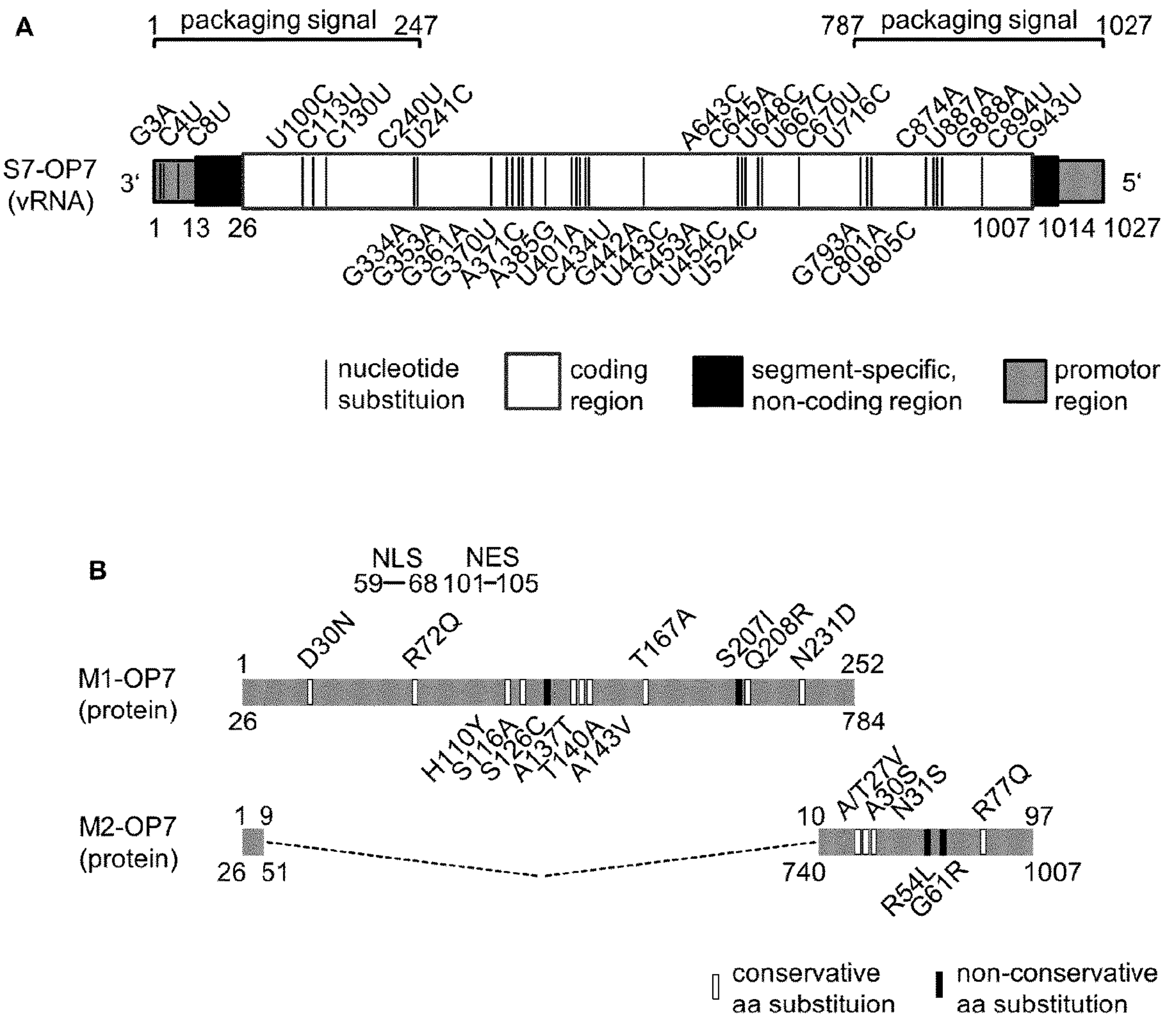
FIG. 1. Alterations in the functional regions of S7-OP7 vRNA. Nucleotide and aa positions are indicated in black numbers, respectively. The 35 constrained nt mutations are depicted.

In a first aspect, the present invention provides an isolated nucleic acid molecule comprising a) SEQ ID No. 2 containing the following substitutions of C3T, G4A, G8A, A100G, G113A, G130A, G240A, A241G, C334T, C353T, C361T, C370A, T371G, T385C, A401T, G434A, C442T, A443G, C453T, A454G, A524G, T643G, G645T, A648G, A667G, G670A, A716G, C793T, G801T, A805G, G874T, A887T, C888T, G894A, G943A, compared to the wild type sequence of SEQ ID No. 1;

b) a nucleotide sequence having greater than 98% identity within the sequence of SEQ ID No. 2;

c) a nucleotide sequence that hybridizes with the nucleotide sequence of a) or b) under stringent conditions;

d) a nucleotide sequence complementary to any of the sequences a), b) or c); or e) mRNA derived from any one of the sequences a), b), c) or d).

In an aspect of the present invention, the nucleic acid molecule according to claim 1 comprising a) SEQ ID No. 3; or b) a nucleic acid sequence having greater than 98% identity with the sequence of SEQ ID No. 3;

c) a nucleotide sequence that hybridizes with the nucleotide sequence of a) or b) under stringent conditions;

d) a nucleotide sequence complementary to any of the sequences a), b) or c); or e) mRNA derived from any one of the sequences a), b), c) or d).

That is, the infection with a virus-like particle, a viral vector, or a virus particle containing the isolated nucleic acid molecule according to the present invention demonstrates an abnormal phenotype compared to wild type virus wherein i) a reduction in the total number of virus particles produced can be determined, ii) a severe reduction in the fraction (percentage) of infectious virus produced, iii) a normal intracellular reproduction of the piRNA while a reproduction of all remaining genome segments apart from the piRNA is reduced, iv) an increased transcription of mRNA from piRNA compared to other genome segments, resulting in v) an enhanced number of proteins, translated from mRNA derived from piRNA, vi) perturbed intracellular trafficking of that protein, leading to a perturbed intracellular trafficking of the ribonucleo-proteins (RNP), vii) a normal incorporation of piRNA into virus particles in comparison to all genome segments of the wild type virus occur, while the incorporation of other genome segments is reduced, and, finally, viii) a stronger induction of the innate immune response expressed by interferon-β expression can be observed. Thus, the isolated nucleic acid molecule according to the present invention, in particular in form of the piRNA demonstrates a strong inhibitory effect on influenza A virus replication, reducing the production of viral components, while favoring its own reproduction and spread.

In an embodiment of the present invention, a nucleic acid molecule is provided having 98% identify, like 98.5%, 99%, 99.5%, 99.6%, or 99.8% of the sequence of Seq. ID No. 2 or Seq. ID No. 3 beside the 35 or 37 mutations described herein compared to the wild type sequence of Seq. ID. No. 1.

In an embodiment of the present invention, the isolated nucleic acid sequence according to the present invention is an isolated nucleic acid sequence having SEQ ID No. 2 or 3 or a functional fragment thereof. In an embodiment of the present invention, the isolated nucleic acid sequence according to the present invention is an isolated nucleic acid sequence having SEQ ID No. 3 containing the 35 substitutions of Seq. ID No. 2 and in addition the substitutions A18G and C535T.

As demonstrated herein, the nucleic acid sequence according to SEQ ID No. 2 as well as SEQ ID No. 3 has the abnormal phenotype described above.

In an embodiment, the nucleic acid molecules according to the present invention further contain the substitutions A18G and C535T, e.g. as shown in SEQ ID No. 3.

Further a nucleic acid molecule is described herein comprising a) SEQ ID No. 1 containing substitutions of at least 20 of the following substitutions of C3T, G4A, G8A, A100G, G113A, G130A, G240A, A241G, C334T, C353T, C361T, C370A, T371G, T385C, A401T, G434A, C442T, A443G, C453T, A454G, A524G, T643G, G645T, A648G, A667G, G670A, A716G, C793T, G801T, A805G, G874T, A887T, C888T, G894A, G943A, b) a nucleotide sequence having greater than 90%, like 95%, 96%, 97%, 98%, 98.5%, 99%, 99.5% identity within the remaining sequence of SEQ ID No. 1 not containing at least one of the substituents as defined in a), c) a nucleotide sequence that hybridizes with the nucleotide sequence of a) or b) under stringent conditions, d) a nucleotide sequence complementary to any of sequences a), b) or c), or e) mRNA derived from any one of sequences a), b), c) or d), or a fragment of a), b), c), d) or e) having the same function with respect to reproduction of virus particle containing the nucleic acid molecule, whereby at least the substitutions at C3T and G8A are present.

The term "or a fragment of a), b), c), d) or e) having the same function with respect to reproduction of virus particle containing the nucleic acid molecule" refers to fragments having the same effect as described for the nucleic acid of SEQ ID No. 2 or SEQ ID No. 3.

Further, the term "or a functional fragment thereof" refers to a nucleic acid molecule having the same effects as described for the nucleic acid molecules of Seq. ID No. 2 or Seq ID. No. 3.

The present inventors recognized that the isolated nucleic acid molecule according to the present invention, in particular an isolated nucleic acid molecule according to the present invention wherein SEQ ID No. 1 containing substitutions of at least 25, at least 30 or all of the substitutions of C3T, G4A, G8A, A100G, G113A, G130A, G240A, A241G, C334T, C353T, C361T, C370A, T371G, T385C, A401T, G434A, C442T, A443G, C453T, A454G, A524G, T643G, G645T, A648G, A667G, G670A, A716G, C793T, G801T, A805G, G874T, A887T, C888T, G894A, G943A demonstrates a protection against influenza infection, whereby at least the substitutions at C3T and G8A are present.

In an embodiment of the present invention, the nucleic acid molecule is in form of an RNA, in particular, the isolated nucleic acid molecule according to the present invention represents a protective interfering RNA (piRNA) derived from genome segment 7 of influenza A. Sequence ID No. 1 as described above refers to the sequence of NCBI reference sequence: NC_002016.1.

The nucleotide sequence may be nucleotide sequence having greater than 98% identity within the sequence of SEQ ID No. 2, for example, the nucleic acid molecule comprises a nucleotide sequence having greater than 98% identity within the sequence of SEQ ID No. 3. The nucleotide sequence may have greater than 99%, 99.5%, 99.6%, 99.7%, 99.8% or 99.9% identity with SEQ ID No. 2. Further, the nucleotide sequence may have greater than 99%, 99.5%, 99.6%, 99.7%, 99.8% or 99.9% identity with SEQ ID No. 3.

The isolated nucleic acid sequence according to the present invention may be obtained from biological systems including cell culture or, alternatively, may be synthesized chemically.

In a further aspect, the present invention relates to a composition comprising the isolated nucleic acid molecule according to any one of the present invention the composition may contain the isolated nucleic acid molecule in combination with a delivery component, e.g. in form of liposomes, exosomes, or other nanoparticles. The skilled person is well aware of providing a suitable composition containing the isolated nucleic acid molecules according to the present invention in a suitable form, e.g. for delivery into a subject.

Said composition may contain additionally the other components of the so called vRNP complex (viral ribonucleoprotein complex), namely, additional viral proteins like PB2, PB1, PA and NP allowing protection against degradation of the piRNA.

In a further aspect, a vector or plasmid comprising the nucleic acid molecule according to the present invention is provided. The vector or plasmid may be any type of vector or plasmid suitable for allowing introduction of the nucleic acid molecule according to the present invention into a host or for multiplication of the isolated nucleic acid molecule.

Suitable vector or plasmid may include expression plasmids for viral proteins like pCAGGS, pcDNA, retroviral vectors like pQXCIP, and double promoter vectors (for recombinant viruses) like pHW2000, pDZ.

In a further aspect, the present invention relates to a virus-like particle, a viral vector, or a virus particle containing the nucleic acid molecule according to the present invention.

The term “viral vector” refers to recombinant infectious viral particles.

The term “virus particle” refers to whole virus being infectious unless attenuated or inactivated.

As used herein, the term “virus-like particle” (VLP) refers to particles comprising the proteins of the envelope and capsid and, in addition, may contain additional genetic material. That is, it may contain at least one nucleic acid molecule, namely, at least the nucleic acid molecule according to the present invention. VLP are non-infectious particles. VLP include DIPs as described above, also referred to as DI virus.

Of course, the virus-like particles may contain other nucleic acid molecules. For example, in case of influenza virus, the virus-like particle or viral vector contains the different segments of genetic material in form of RNA, e.g. in form of the vRNP complex described above, while the viral capsid or viral envelope is composed of proteins derived from influenza A or other virus including influenza B and influenza C.

Also non-structural viral proteins may be present or absent in the virus-like particle or viral vector according to the present invention.

In an embodiment of the present invention, the virus-like particle or the viral vector is derived from an influenza virus, in particular, influenza A virus. Further, the virus particle is an influenza virus, like an influenza A virus. That is, in an embodiment of the present invention, the viral vector or the virus particle is an influenza A virus containing the nucleic acid sequence according to the present invention, in particular, the nucleic acid sequence being an RNA-molecule of SEQ ID No. 2 or 3 as segment 7 optionally together with the other segments 1 to 6 and 8 of influenza A virus.

The virus-like particle, the viral vector or the virus particle is particularly useful as a medicament. That is, in a further aspect, the present invention relates to the use of the virus-like particle, the viral vector or the virus particle as a medicament. This medicament or pharmaceutical composition, which is used herein interchangeably, may be in form of a vaccine allowing prophylactic or therapeutic treatment, e.g. in form of vaccination of an individual.

The virus-like particle, the viral vector or the virus particle according to the present invention is particularly useful in the treatment of a viral infection. In particular, it is useful in the treatment of a viral infection with a virus having at least parts of the envelope proteins of an infectious virus, like HA or NA, and, in addition, the virus-like particle, the viral vector or the virus particle contains the nucleic acid molecule according to the present invention.

Using the virus-like particle, the viral vector or the virus particle in the treatment of a viral infection, it is possible to reduce the total number of virus particles produced and, in addition, a remarkable reduction in the fraction of infectious virus particles produced is possible.

Thus, it is possible to inhibit replication of the infectious virus particles using the viral vector, virus-like particle or the virus particle according to the present invention by reducing the production of the virus particle.

In a further embodiment, the present invention refers to a host cell containing the nucleic acid vector or plasmid according to the present invention containing the nucleic acid molecule according to the present invention. These host cells allow to produce the nucleic acid molecules according to the present invention. Production and culturing of host cells as well as suitable host cells are known to the skilled person, e.g. in cell culture or eggs.

In a further aspect, the present invention relates to a pharmaceutical composition containing a virus-like particle, a viral vector, or a virus particle according to the present invention, a nucleic acid molecule according to the present invention, a composition according to the present invention, a vector or plasmid according to the present invention and/or a host cell according to the present invention.

The pharmaceutical composition is particular useful as a therapeutic or, in particular, as a prophylaxis vaccine. In particular, the pharmaceutical composition according to the present invention is for use and the treatment of a viral infection, in particular, whereby said viral infection is caused by virulent influenza virus, like influenza A virus. That is, nucleic acid molecules according to the present invention, the virus-like particle, a viral vector, or a virus particle according to the present invention, a nucleic acid molecule according to the present invention, a composition according to the present invention, a vector or plasmid according to the present invention and/or a host cell according to the present invention represents suitable antiviral agents.

The pharmaceutical composition according to the present invention is adapted for administration to an individual being an animal or human. In an embodiment, the animal is selected from pig, horse, dog, cat or bird. In another embodiment, the individual is a human.

For example, the pharmaceutical composition is adapted for administration by the mucosal route, like the intranasal administration, orally. Alternatively, the administration may be conducted by intravenous administration, intramuscular administration or subcutaneous administration.

The pharmaceutical composition may contain additionally suitable diluents, carrier or effluence. The skilled person is well aware of suitable diluents, effluents or carriers accordingly.

Further, the present invention relates to a vaccine for vaccination against viral infection, in particular, influenza viral infection. The vaccine contains a nucleic acid molecule according to the present invention, a composition according to the present invention, a vector or plasmid according to the present invention and/or a virus-like particle, viral vector, or a virus particle according to the present invention.

In an embodiment, the nucleic acid molecule is a RNA molecule. In another embodiment, the influenza viral infection is influenza A viral infection. The vaccination may typically be a prophylactic vaccination but also a therapeutic vaccination is possible.

It has been recognized that the pharmaceutical composition according to the present invention, e.g. the vaccine according to the present invention as well as the virus-like particle, the viral vector or the virus particle according to the present invention allows to deliver immune protection in an individual.

That is, due to the surprising properties of the protective interfering nucleic acid molecule according to the present invention, in particular, the protective interfering RNA molecule according to the present invention as described herein, the percentage of infectious virus particle can be reduced and, in addition, a spread of the infectious virus can be reduced or inhibited while the reproduction and spread of the virus-like particle, the viral vector, or the virus particle containing the nucleic acid molecules according to the present invention is increased in the individual.

Thus, the viral infection can be controlled and reduced accordingly.

Hence, in a further aspect of the present invention, the present invention relates to a method of prophylactic or therapeutic treatment of virus infection, in particular, influenza virus infection, like influenza A virus infection. Said method includes the administration of the nucleic acid molecules according to the present invention, the composition according to the present invention, the virus-like particle, the viral vector, or the virus particle according to the present invention or the pharmaceutical composition according to the present invention to an individual afflicted with virus infection or supposed to be afflicted with virus infection or for prophylactic vaccination. Administration of the same may be if affected once or several times.

The way of administration may be as described above.

Finally, the present invention relates to a composition or kit comprising the virus-like particle, the viral vector or the virus particle according to the present invention, or a nucleic acid molecule according to the present invention, or a composition according to the present invention, or a vector plasmid according to the present invention, or a host cell according to the present invention and, in addition, a wild type viral vector or a wild type virus particle. The composition or kit according to the present invention is useful for vaccination and therapeutic or prophylactic treatment of virus infection.

In an embodiment, the wild type viral vector is an influenza viral vector, like influenza A viral vector. The wild type virus particle may be an influenza virus particle, like influenza A virus particle.

The composition or kit according to the present invention may be in form of a pharmaceutical composition useful in the treatment or protecting against viral infection.

The invention will be described further by the way of examples without limiting the same.

Examples

Figure 3:
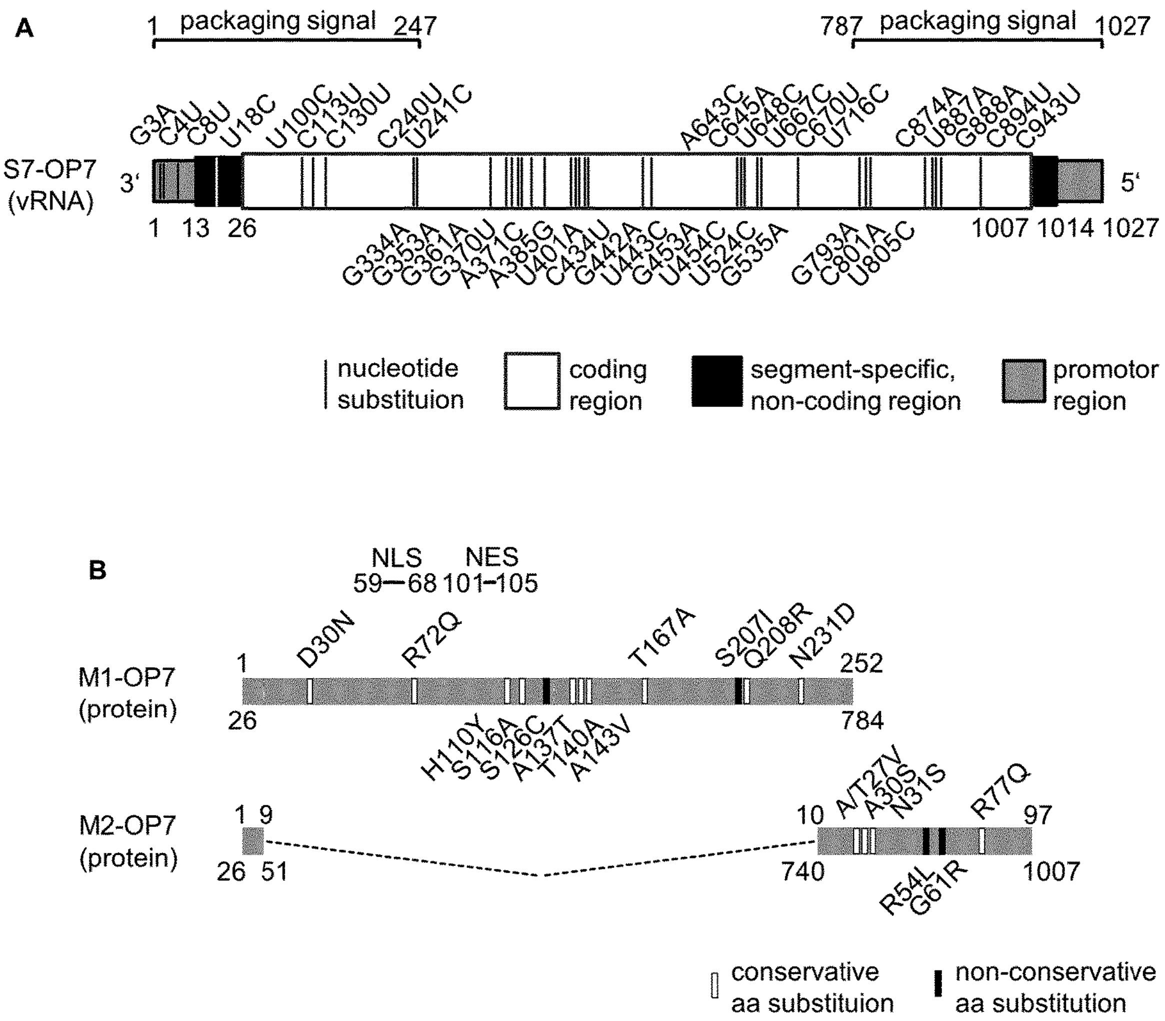
FIG. 3. Alterations in the functional regions of S7-OP7 vRNA. Nucleotide and aa positions are indicated in black numbers, respectively. All 37 nt mutations (in relation to the RefSeq, i.e. Seq. ID No. 1) are depicted.

In the present study, we performed single-cell infection experiments. Surprisingly, a fraction of the infected single cells showed an unusual phenotype, characterized by a low infectious titer of the viral progeny and an over-proportional intracellular quantity of S7 vRNA in relation to other genome segments, which was caused by the co-infection of a subpopulation of viruses, in the following termed Over-Proportional S7 (OP7) virus. Followed by its enrichment, we determined the sequence of the genomic vRNA of S7 from OP7 virions (S7-OP7) that shows 35 mutations as shown in FIG. 1 and the 37 mutations as shown in FIG. 3, respectively, in relation to the wild-type (WT) sequence, affecting the promotors, the encoded matrix protein 1 (M1) and 2 (M2) and the genome packaging signals. Furthermore, cell population-based infection experiments with OP7 seed viruses show that (i) the altered viral RNA synthesis can be accounted for by the "superpromotor" (Belicha-Villanueva et al., 2012, Recombinant influenza A viruses with enhanced levels of PB1 and PA viral protein expression. J Virol 86, 5926-5930) identified on S7-OP7, (ii) the released OP7 virions are defective in virus replication due their incomplete vRNA content, except for S7, which was predominantly incorporated and (iii) the enhanced nuclear accumulation of the mutated M1 protein may cause the partial nuclear retainment of all genome segments. Finally, co-infection experiments demonstrated a strong interference of OP7 virus with replication of relevant homologous and heterologous IAV strains, and interference in human cell lines, which may render them promising for utilization as an antiviral agent. Moreover, our results unveil that OP7 virions are yet unrecognized form of DIPs, derived from IAVs, with a non-deleted but mutated genomic RNA segment.

Cells and Viruses

MDCK cells (ECACC, #84121903) were cultivated in Glasgow Minimum Essential Medium (GMEM) with 10% fetal bovine serum (FBS) and 1% peptone. HEK 293 and A549 cell lines were maintained in Dulbecco's Modified Eagle's Medium (DMEM) containing 10% FBS. All cultivations and infections were performed at 37° C. in a 5% $CO_2$ atmosphere. Infection media was prepared by adding porcine trypsin to a final concentration of 5 BAEE U/mL to the corresponding serum-free medium. Influenza virus strain PR8 was provided by RKI (#3138) and NIBSC (#99/716). Strain H3N2 (#15/192) and H1N1-pdm09 (#10/122) were supplied by NIBSC. Seed virus titers were determined by standard $TCID_{50}$ assay using MDCK cells (Genzel and Reichl, 2007, Vaccine production—state of the art and future needs in upstream processing. In Methods in biotechnology: animal cell biotechnology, R. Pörtner, ed. (Totowa, N.J.: Humana Press Inc.), pp. 457-473) and MOIs were based on this titer.

Isolation of Single Infected Cells

Isolations were performed as described previously (Heldt et al., 2015, Single-cell analysis and stochastic modelling unveil large cell-to-cell variability in influenza A virus infection. Nat Commun 6, 8938). In brief, confluent MDCK cells in 9.6 $cm^2$ dishes were infected at indicated MOIs in 250 μL of infection media. During the first hour of incubation, the dish was rocked. The medium volume was then increased to 2 mL and cells were incubated for another 1.5 h. After washing (twice) with phosphate buffered saline (PBS), cells were trypsinized for 10-15 min. Trypsinization was stopped using cell maintenance media (containing 10% FBS). The homogenized cell suspension was serially diluted in pre-warmed (37° C.) infection media. Subsequently, 50 μL of the diluted cell suspension (concentration: one cell per 50 μL) were quickly added to each well of a pre-warmed 384-well plate (Greiner, #781901) using an electronic multichannel/multistep pipet. Plates were incubated until 12 hpi. After brief centrifugation at 150×g, we identified individual wells containing single cells by phase-contrast microscopy. Supernatants were straightaway subjected to plaque assays to quantify virus yields. Remaining single cells were washed with PBS and 5 μL of a diluted bovine serum albumin (BSA) solution (Thermo Scientific, #B14) at a concentration of 1 mg/mL was added to the wells. The 384-well plate was sealed and immediately stored at −80° C. until real-time RT-PCR.

Plaque Assay

Complete supernatants of infected single cells were investigated for the virus titer (PFU/cell) using two dilutions (either 90% or 10% of the total sample). 250 μL of each dilution was incubated on MDCK cells in 6-well plates for 1 h. During incubation, the plate was rocked. After removal of the supernatant, cells were overlaid with 1% agar (in infection medium) and incubated for 4 days. Cells were then fixed with methanol and stained using a 0.2% crystal violet solution. Plaque count was determined using light microscopy.

Cell Population-Based Infection and Sampling

Confluent cells in 9.6 $cm^2$ dishes were infected at indicated MOIs in 250 μL of infection medium. During 1 h of incubation, the dish was rocked. Inoculum was removed, cells were washed twice with PBS and 2 mL of infection media was added. For each investigated time point post infection, one dish was sampled.

Aliquots of supernatants were stored at −80° C. until virus titration or the purification of vRNA in the released virions using "NucleoSpin RNA Virus" kit (Macherey-Nagel) according to the manufacturers' instructions. Remaining cells were then washed twice with PBS. Lysis of cells and intracellular RNA extraction was performed using "NucleoSpin RNA" kit (Macherey-Nagel). Purified vRNAs from virus particles, and intracellular vRNA, mRNA and cRNA were quantified by real-time RT-qPCR. The viral RNA levels per cell were calculated based on the cell count at time point of infection.

Virus Quantification

Virus titers of cell population-based infections were determined based on standard $TCID_{50}$ assay using MDCK cells (Genzel and Reichl, 2007, see above) and HA assay (Kalbfuss et al., 2008, Monitoring influenza virus content in vaccine production: precise assays for the quantitation of hemagglutination and neuraminidase activity. Biologicals 36, 145-161). HA titers were expressed as $\log_{10}$ HA units per test volume ($\log_{10}$ HAU/100 μL). Virus particle concentrations $c_{virus}$ (virions/mL) were calculated, assuming that agglutination occurs up to a dilution in which the number of virions equals the number of erythrocytes (Burleson et al., 1992, Hemagglutination Assay. In Virology—A Laboratory Manual (Academic Press), pp. 86-92). Thus, the calculation was based on the HA titer and the cell concentration of the erythrocyte suspension ($2\times10^7$ cells/mL).

$$c_{virus}=2\times10^7\times10^{(\log_{10} HAU/100\ \mu L)}$$

Real-Time RT-qPCR

Real-time RT-qPCR was utilized for absolute quantification of: (i) intracellular vRNA of single-cell samples, (ii) intracellular vRNA, mRNA and cRNA of cell population-derived samples, and (iii) purified vRNA from virus particles. For this, we derived a primer combination from a previously published method (Kawakami et al., 2011, Strand-specific real-time RT-PCR for distinguishing influenza vRNA, cRNA, and mRNA. J Virol Methods 173, 1-6) that enables polarity- and gene-specific amplification of individual IAV RNAs. A tagged primer (Table 1) was used for reverse transcription (RT), qPCR primers are listed in Table 2. To facilitate absolute quantification, we generated RNA reference standards and numbers of viral RNAs were calculated based on calibration curves.

TABLE 1

Tagged Primers for RT (Related to Real-Time RT-qPCR)

| Target | RNA Type | Primer Name | Sequence (5' -> 3') |
|---|---|---|---|
| Segment 5 | vRNA | S5 tagRT for | ATTTAGGTGACACTATAGAAGCGAGTGATTATGAGG-GACGGTTGAT (SEQ ID No. 4) |
| | cRNA | S5 tagRT rev | GCTAGCTTCAGCTAGGCATC AGTAGAAACAAGGGTATTTTT-CTT (SEQ ID No. 5) |
| Segment 7 | vRNA | S7 tagRT for | ATTTAGGTGACACTATAGAAGCGAGCCGA-GATCGCACAGAGACTT(SEQ ID No. 6) |
| | cRNA | S7 tagRT rev | GCTAGCTTCAGCTAGGCATCAGTAGAAACAAGGTAGTTTTT-TAC(SEQ ID No. 7) |
| Segment 8 | vRNA | S8 tagRT for | ATTTAGGTGACACTATAGAAGCGGATAGTGGAGCGGATT-CTG(SEQ ID No. 8) |
| | cRNA | S8 tagRT rev | GCTAGCTTCAGCTAGGCATC AGTAGAAACAAGGGTGTTTTT-TAG (SEQ ID No. 9) |
| Segment 5, 7 and 8 | mRNA | Oligo tagdTRT | GTAAAACGACGGCCAGTTTTTTTTTTTTTTTTT (SEQ ID No. 10) |

TABLE 2

Primers for qPCR (Related to Real-Time RT-qPCR)

| Target | RNA Type | Primer Name | Sequence (5' -> 3') |
|---|---|---|---|
| Introduced tag sequence | vRNA | vRNA tagRealtime for | ATTTAGGTGACACTATAGAAGCG (SEQ ID No. 11) |
| | cRNA | cRNA tagRealtime rev | GCTAGCTTCAGCTAGGCATC (SEQ ID No. 12) |
| | mRNA | mRNA tagRealtime rev | GTAAAACGACGGCCAGT (SEQ ID No. 13) |
| Segment 5 | vRNA | Seg 5 Realtime rev | CGCACTGGGATGTTCTTC (SEQ ID No. 14) |
| | cRNA and mRNA | Seg 5 Realtime for | GGAAAGTGCAAGACCAGAAGAT (SEQ ID No. 15) |
| Segment 7 | vRNA | Seg 7 Realtime rev | TGAGCGT-GAACACAAATCCTAAAA (SEQ ID No. 16) |
| | cRNA and mRNA | | CATTGGGATCTTGCACTTGA-CATT (SEQ ID No. 17) |
| Segment 8 | vRNA | Seg 8 Realtime rev | CACTTTCTGCTTGGGTATGA (SEQ ID No. 18) |
| | cRNA and mRNA | | GGCGGGAACAATTAGGTCAGA (SEQ ID No. 19) |

For in vitro synthesis of the reference standards, we used plasmids carrying the complete sequence of vRNA, mRNA and cRNA (of the corresponding segments) in a conventional PCR using "Phusion High-Fidelity DNA Polymerase" (Thermo Scientific) according to the manufacturers' instructions. Thereby, the primers (Table S3) introduced a T7 promoter sequence (in the desired orientation) into the PCR products. After purification ("InnuPrep PCRpure Kit" (Analytik Jena)), we used the PCR products for in vitro transcription ("TranscriptAid T7 High Yield Transcription Kit" (Thermo Scientific)). Final purification of the RNA reference standards was conducted using "NucleoSpin RNA Clean-up" (Macherey-Nagel); standards were stored at −80° C. until use.

For RT, we mixed 1 μL of the RNA sample with 0.5 μL of dNTPs (10 mM) and 0.5 μL of the RT primer (10 μM for mRNA primer, or 1 μM for vRNA and cRNA primer), and filled up to 6.5 μL with nuclease-free water. Incubation was performed at 65° C. for 5 min and then 5 min at different temperatures: 42° C. for mRNA, or 55° C. for vRNA and cRNA measurements. During the latter step, we added a pre-warmed mixture (42° C. for mRNA, or 55° C. for vRNA and cRNA measurements) consisting of 2 μL "5×RT buffer", 0.25 μL (50 U) "Maxima H Minus Reverse Transcriptase" and 1.25 μL nuclease-free water (all reagents from Thermo Scientific). RT was conducted for 30 min at 60° C., followed by termination at 85° C. for 5 min. In addition, we reverse transcribed RNA reference standards in 10-fold diluted steps: 1 to $1\times10^{-7}$ ng. Each of this reaction contained (optionally) cellular total RNA (to conform with intracellular RNA samples): (i) 350 fg for single-cell-, (ii) 350 ng for population-based measurements, and (iii) no total RNA for measurements of vRNA from purified virions. The cDNA reaction products were then diluted to 20 μL in nuclease-free water and stored at −20° C., or immediately subjected to qPCR analysis.

For qPCR, we used the "Rotor-Gene Q real-time PCR cycler" (Qiagen). The qPCR mix (10 μL) contained 1×"Rotor-Gene SYBR Green PCR Kit" (Qiagen), 500 nM of each primer and 3 μL of diluted cDNA. Initial denaturation was conducted at 95° C. for 5 min, followed by 40 PCR cycles (two-step protocol): 95° C. for 10 s, and 62° C. for 20 s. Afterwards, melting curve analysis was performed from 65 to 90° C.

Absolute Quantification of Viral RNAs

To calculate absolute quantities of viral RNAs, we plotted the $c_T$ values (from qPCR) of the serially 10-fold diluted RNA reference standards (ordinate) against the $\log_{10}$ number of RNA molecules $n_{molecules}$ (abscissa) to generate calibration curves (linear regression). $n_{molecules}$ was calculated based on the quantity of the standard $m_{STD}$ (ng), the fragment length Nbases (bp), the average mass of one base (k=340 (Da/bp)), and the Avogadro constant $N_A$ ($mol^{-1}$).

$$n_{(molecules)} = \frac{m_{STD}}{N_{bases} \times k \times N_A^{-1} \times 10^9}$$

Using the $c_T$ value of a sample, the number of viral RNA molecules $Q_{sample}$ was calculated by considering the slope (m) and y-intercept (b) of the calibration curve, the coefficient of dilution of the RT reaction $F_{RT}$, and the total volume of the RNA sample $V_{sample}$ (μL).

$$Q_{sample} = 10^{\left(\frac{c_T - b}{m}\right)} \times F_{RT} \times V_{sample}$$

Segment-Specific PCR

Purified vRNAs from virions were subjected to RT-PCR for two different purposes: (i) investigation of the presence of subgenomic RNAs and (ii) the determination of vRNA sequence (described in more detail below). For RT, we used a universal "Uni12" primer (Hoffmann et al., 2001, Universal primer set for the full-length amplification of all influenza A viruses. Arch Virol 146, 2275-2289), which hybridizes to the conserved 3' end of all eight genome segments, to synthesize all cDNAs in one reaction. In subsequent polymerase chain reaction (PCR), we used individual reactions for each segment. The primer sequences (Table 3) comprise the conserved 3' or 5' terminal vRNA end in conjunction with a segment-specific portion to allow for the specific amplification of the complete genome segment. Please note that for sequencing of S7-OP7 vRNA, we used adapted primers (Table 3).

TABLE 3

Primers (Related to Segment-Specific RT-PCR)

| Reaction | Target | Primer Name | Sequence (5' -> 3') |
|---|---|---|---|
| RT | All segments (wt) | Uni12 | AGCAAAAGCAGG (SEQ ID No. 20) |
| | Segment 7 (OP7 Virus) | S7-OP7 RT | AAGCAGGTAGATATTGAAAG (SEQ ID No. 21) |
| | Segment 1 | S1 Uni for | AGCGAAAGCAGGTCAATTAT (SEQ ID No. 22) |
| | | S1 Uni rev | AGTAGAAACAAGGTCGTTTTTAAAC (SEQ ID No. 23) |
| | Segment 2 | S2 Uni for | AGCGAAAGCAGGCAAACCAT (SEQ ID No. 24) |
| | | S2 Uni rev | AGTAGGAACAAGGCATTTTTTCATG (SEQ ID No. 25) |
| | Segment 3 | S3 Uni for | AGCGAAAGCAGGTACTGATCC (SEQ ID No. 26) |
| | | S3 Uni rev | AGTAGAAACAAGGTACTTTTTTGG (SEQ ID No. 27) |
| | Segment 4 | S4 Uni for | AGCAAAAGCAGGGGAA (SEQ ID No. 28) |
| | | S4 Uni rev | AGTAGAAACAAGGGTGTTTT (SEQ ID No. 29) |
| PCR | Segment 5 | S5 Uni for | AGCAAAAGCAGGGTAGATAATC (SEQ ID No. 30) |
| | | S5 Uni rev | AGTAGAAACAAGGGTATTTTTC (SEQ ID No. 31) |
| | Segment 6 | S6 Uni for | AGCGAAAGCAGGGGTTTAAAATG (SEQ ID No. 32) |
| | | S6 Uni rev | AGTAGAAACAAGGAGTTTTTTGAAC (SEQ ID No. 33) |
| | Segment 7 | S7 Uni for | AGCGAAAGCAGGTAGATATTG (SEQ ID No. 34) |
| | | S7 Uni rev | AGTAGAAACAAGGTAGTTTTTTAC (SEQ ID No. 35) |
| | Segment 7 (OP7 Virus) | S7-OP7 PCR for | AAGCAGGTAGATATTGAAAG (SEQ ID No. 36) |
| | | S7-OP7 PCR rev | AGTAGAAACAAGGTAGTTTT (SEQ ID No. 37) |
| | Segment 8 | S8 Uni for | AGAAAAAGCAGGGTGACAAA (SEQ ID No. 38) |
| | | S8 Uni rev | AGTAGAAACAAGGGTGTTTT (SEQ ID No. 39) |

For RT, 10 µL of RNA was mixed with 1 µL dNTPs (10 mM) and 1 µL primer (10 mM), and filled up to 14.5 µL with nuclease-free water. Incubation was conducted at 65° C. for 5 min and 4° C. for 5 min. We then added 4 µL of “5×Reaction Buffer”, 50 U (0.5 µL) “RevertAid H Minus Reverse Transcriptase”, 20 U (0.5 µL) “RiboLock RNase Inhibitor” and 0.5 µL nuclease-free water (all reagents from Thermo Scientific), and incubated at 42° C. for 60 min. RT was terminated at 70° C. for 10 min. cDNA was stored at −20° C., or immediately subjected to PCR.

For PCR, 2 µL cDNA was combined with 4 µL “5× Phusion HF Buffer”, 2 µL $MgCL_2$ (10 mM), 1 µL dNTPs (10 mM), 1 µL of each primer (10 µM), 0.2 µL (0.4 U) “Phusion DNA Polymerase” and 8.8 µL nuclease-free water (all reagents from Thermo Scientific). Initial denaturation was performed at 98° C. for 3 min, followed by 25 PCR cycles: 98° C. for 25 s, 54° C. for 45 s, and 72° C. for different times: 2 min for S1-S3, 1.5 min for S4-S6, and 1 min for S7 and S8. Final elongation was conducted at 72° C. for 10 min. PCR products were then visualized using agarose gel electrophoresis.

Determination of vRNA Sequences

We determined the sequence of the purified vRNA from virions. For sequencing of the coding regions, we used the segment-specific PCR (as described above) to amplify the complete segments. After purification, the PCR products were sequenced using the same PCR primers. All sequencing reactions were conducted by Eurofins Genomics (Ebersberg, Germany) utilizing Sanger sequencing.

For sequencing of the terminal vRNA ends, we derived a modified procedure from a previously published method (de Wit et al., 2007, Rapid sequencing of the non-coding regions of influenza A virus. J Virol Methods 139, 85-89), which is based on the circularization of vRNA using a RNA ligase.

The subsequent amplification of the junction region (containing the vRNA ends) was performed by RT-PCR. For the RT, a random hexamer primer was used. In subsequent PCR (primers are listed in Table S5), we used a segment-specific primer in combination with a second primer, which was designed across the junction of the 3' and 5' vRNA end. For sequencing of each 3' and 5' end, we used one primer pair. Note that sequences of the terminal 2 bp of each vRNA end were not determined (due to the primer design).

Circularization was performed by mixing 11.5 μL of RNA sample with 4 μL (40 U) of "T4 RNA Ligase 1", 2 μL of "10×T4 RNA Ligase Reaction Buffer", 2 μL of a 10 mM ATP solution (all reagents from New England BioLabs) and 0.5 μL (20 U) of "RiboLock RNase Inhibitor" (Thermo Scientific). The mixture was incubated for 1 h at 37° C., followed by heat inactivation at 65° C. for 15 min. We immediately reverse transcribed the circularized RNA.

For RT, a reaction mixture containing 4 μL ligated RNA, 1 μL (0.2 μg) of "Random Hexamer Primer", 1 μL of dNTPs (10 mM) and 8.5 μL of nuclease-free water was incubated at 65° C. for 5 min (all reagents from Thermo Scientific) and immediately transferred on ice. We then added 4 μL of "5×RT buffer", 0.5 μL (100 U) "Maxima H Minus Reverse Transcriptase", 0.5 μL (20 U) of "RiboLock RNase Inhibitor" and 0.5 μL of nuclease-free water (all reagents from Thermo Scientific). Incubation was conducted at 25° C. for 10 min and then 50° C. for 30 min. Termination was performed at 85° C. for 5 min. cDNA was stored at −20° C. or immediately subjected to PCR.

The PCR reaction mix consisted of 4.5 μL of the RT product, 6 μL "5× Phusion HF Buffer", 3 μL $MgCL_2$ (10 mM), 1.5 μL dNTPs (10 mM), 1.5 μL of each primer (10 μM), 0.3 μL (0.6 U) "Phusion DNA Polymerase" and 11.7 μL of nuclease-free water (all reagents from Thermo Scientific). The cycling conditions comprised initial denaturation for 105 s at 98° C., and then 40 PCR cycles: 10 s at 98° C., 30 s at 60° C. and 40 s at 72° C. Final elongation was conducted at 72° C. for 10 min. All PCR products were excised from gels (after agarose gel electrophoresis) and then purified using the "QIAquick Gel Extraction Kit" (Qiagen) according to the manufacturers' instructions.

Analysis of Innate Immune Response

Expression of IFN-beta and Mx1 of infected cell populations was assessed using real-time RT-qPCR. For this, 500 ng of purified intracellular RNA was reverse transcribed using an oligo(dT) primer and "Maxima H Minus Reverse Transcriptase" (both from Thermo Scientific) according to the manufacturers' instructions. Subsequently, we performed a qPCR with "Rotor-Gene Q real-time PCR cycler" (Qiagen). The qPCR mix (10 μL) contained 1×"Rotor-Gene SYBR Green PCR Kit" (Qiagen), 500 nM of each primer and 3 μL of diluted cDNA. Initial denaturation was conducted at 95° C. for 5 min, followed by 40 PCR cycles (two-step protocol): 95° C. for 10 s, and 62° C. for 20 s. Gene expression was expressed as fold induction (over mock-infected cells) and calculated using the delta-delta $c_T$ method with 18s rRNA as reference gene.

Analysis of Intracellular Viral Proteins

At indicated time points, infected MDCK cell populations were washed twice with PBS. We then added 150 μL of radioimmunoprecipitation assay (RIPA) buffer. Cells were harvested using a cell scraper and homogenized using 0.2 μm syringes. After centrifugation (10,000×g, 10 min and 4° C.), aliquots of supernatants were stored at −80° C. until western blot (WB) analysis. For WB, we used a polyvinylidene difluoride (PVDF) membrane. Mouse anti-NP monoclonal antibody (mAb) (Abcam, #ab128193) was used at a dilution of 1:2,000, rabbit anti-PA polyclonal antibody (pAb) (GeneTex, #GTX125932) was diluted to 1:10,000, mouse anti-M1 mAb (AbD serotech, #MCA401) was used at a dilution of 1:1,000 and mouse anti-glyceraldehyde 3-phosphate dehydrogenase (GAPDH) mAb from Merck (#CB1001) was diluted to 1:5,000. Secondary antibody stainings were performed using donkey anti-mouse pAb conjugated with horseradish-peroxidase (HRP) (Jackson ImmunoResearch, #715-036-151) and HRP-conjugated goat anti-rabbit pAb (Jackson ImmunoResearch, #111-035-003), both at a dilution of 1:10,000. Proteins on the blots were visualized using "SuperSignal West Dura Extended Duration Substrate" (Thermo Scientific).

Electron Microscopy

Virus particles released in cell population-derived infections were inactivated using β-propiolactone and then visualized utilizing ns-TEM. The samples were bound to a glow discharged carbon foil covered grid and stained using 1% uranyl acetate. Grids were imaged at room temperature using a "CM-120 BioTwin" transmission electron microscope (Philips). Images were acquired using a "TemCam-F416 CMOS" camera (TVIPS).

Imaging Flow Cytometric Analysis

At indicated time points post infection, we rocked the population of infected MDCK cells to release detached cells into the infection media. The supernatant was harvested and detached cells were separated from the supernatant by centrifugation (300×g, 10 min and 4° C.). Remaining adherent cells were trypsinized and afterwards combined with the detached cells from the previous step. Cells were then fixed with paraformaldehyde at a final concentration of 1% (30 min and 4° C.) and washed with PBS. Aliquots were stored in 70% ethanol at −20° C. until imaging flow cytometric analysis.

Analysis was performed as described previously (Frensing et al., 2016, Defective interfering viruses and their impact on vaccines and viral vectors. Biotechnol J 10, 681-689). In brief, cell samples were washed twice with PBS containing 0.1% BSA and 2% glycine, thereby using centrifugation at 300×g for 10 min at 4° C. Samples were then blocked for 30 min at 37° C. in PBS containing 1% BSA. After washing, we performed antibody incubations (always at 37° C. for 1 h in the dark). Monoclonal mouse anti-NP antibody mAb61A5 (a gift from Fumitaka Momose) was used at a dilution of 1:500. The antibody preferentially binds to NP in the conformation inherent to the vRNP complex (Momose et al., 2007, Visualization of microtubule-mediated transport of influenza viral progeny ribonucleoprotein. Microbes Infect 9, 1422-1433). Subsequent to washing, the secondary Alexa Fluor 647-conjugated goat anti-mouse pAb (LifeTechnologies, #A21235) was used at a dilution of 1:500 and cells were then washed two times. Nuclei were visualized by adding DAPI.

For M1 staining, we used a FITC-conjugated mAb mouse anti-M1 (AbD serotec, #MCA401FX) at a dilution of 1:100. After cells were washed, they were resuspended in 1 mL of PBS. We then added 5 μL PureLink RNase A (LifeTechnologies) for RNA degradation and 0.5 μL of 7-AAD (Merck) for nuclear staining. Incubation was conducted for 30 min at room temperature in the dark. Finally, cells were washed. ImageStream X Mark II (Amnis, EMD Millipore) was used for acquisition of 10,000 cells per sample (debris and cell doublets were excluded) at 60× magnification. The 375 and 642 nm lasers were utilized for excitation of the vRNP-/DAPI-stained samples, and the signal from channel 1 (CH1) and 5 (CH5) were acquired along with the brightfield (BF) imagery on CH6. For M1-/7-AAD-stained cells, we used the 488 and 561 nm excitation lasers and for detection CH2 and CH5 with BF on CH6. Single-stained positive controls were used to adjust laser powers and to acquire compensation files.

We used IDEAS software (version 6.1) for image analysis, using only in-focus single cells for analysis. Subcellular localization of vRNPs was assessed by calculating percentages of fluorescence intensity (FI) of the vRNP signal that was co-localized with the nuclear signal (derived from DAPI). For this, the masks "nucleus" and "whole cell" were created using function "morphology" (on CH1 imagery) and "object" (on CH6), respectively. New features were generated, termed "intensity CH5 nucleus" and "intensity CH5 whole cell", by using the feature "intensity" on CH5, within the mask "nucleus" and "whole cell", respectively. A new combined feature "FI in nucleus" was created with the following definition: "intensity CH5 nucleus"/"intensity CH5 whole cell". CH1- and CH5-double positive cells (of focused, single cells) were plotted on histograms using this feature. The fraction of FI in the nucleus (%) was calculated by multiplying the mean values of said feature by 100. M1 localization was assessed the same way, but under consideration of the corresponding detection channels.

Single-Cell Analysis Indicates Presence of a Viral Subpopulation with Unusual Phenotype in PR8 Virus To study the dependency of virus release on intracellular S7 vRNA quantity, which showed a large cell-to-cell variability, we performed single-cell analysis of infected cells. A population of adherent Madin-Darby canine kidney (MDCK) cells was infected with IAV and then trypsinized to obtain a cell suspension. The diluted cell suspension was transferred to a 384-well plate to obtain (on average) one cell per well, and wells containing single cells were identified by phase-contrast microscopy. At 12 hpi. we quantified virus titers from these cells using the plaque assay. In addition, cells were lysed and analyzed for intracellular vRNAs by real-time reverse transcription quantitative PCR (RT-qPCR). Infection experiments were here performed with strain influenza virus A/Puerto Rico/8/34 (PR8) from the National Institute for Biological Standards and Control (PR8-NIBSC), or from Robert-Koch-Institut (PR8-RKI).

Surprisingly, upon infection with PR8-NIBSC at a multiplicity of infection (MOI) of 10, individual cells that show a low infectious virus titer contained a relatively high and disproportionate level of S7 vRNA in relation to S5 or S8. In particular, cells showing no plaque titer (Zero plaque-forming units (PFU)) almost exclusively contained this over-proportional quantity of the S7 segment. Most of the cells that released 1-10 PFU contained such levels as well. Furthermore, the distribution of virus titers between single cells appeared to be bimodal, as two subpopulations of cells can be observed, including a subset that released about 1-10 PFU. In addition, it seemed that cells with over-proportional S7 level contained a different S7 vRNA sequence (compared to cells with equimolar ratios) as indicated by different denaturation temperatures of S7 amplicons in melting curve analysis. Thus, it has been hypothesized that PR8 NIBSC may contain a subpopulation of virions with a different S7 segment.

To test whether such a subpopulation was also present in a different seed virus, we infected cells with PR8-RKI at an MOI of 10. However, no such an unusual behaviour was observed for S7. We neither observed over-proportional levels of S7 vRNA in comparison to S5 or S8, nor did we recognize any bimodality in the histogram of virus titer. Concurrently, the fraction of cells showing no virus release was very low for PR8-RKI virus replication (only 3% in compared to 43% for the infection with PR8-NIBSC virus).

OP7 Virus Subpopulation can be Enriched Using Single-Cell Infection Experiments and Depleted by Plaque Purification To investigate whether we can enrich the putative viral subpopulation in the PR8-NIBSC seed virus, we performed single-cell infection experiments at an MOI of 10 (as described above), and progeny virions in the supernatants of individual cells were expanded using confluent MDCK cells. All seed viruses were titrated for subsequent single-cell experiments at an MOI of 10.

Indeed, infection experiments with some of the single-cell derived virus seeds showed a strongly pronounced unusual phenotype. In particular, the infected cells exclusively contained an over-proportional level of S7 vRNA in relation to S5 or S8. These viruses are here referred to as "OP7 seed virus". Moreover, 93% of cells infected with OP7 seed virus number 1 (OP7-1) showed no virus release, while for OP7-2 and OP7-5, the fraction was 95% and 90%, respectively. The remaining cells produced very low virus titers (1-10 PFU). Of the 55 single-cell derived virus seeds (obtained in four independent experiments), only five virus seeds showed the desired phenotype.

OP7 Virions are Non-Infectious Due to their Incomplete vRNA Content, Except for S7, which Predominates in the Virions As OP7 virus was successfully enriched, we next performed cell population-based experiments to explore additional features of OP7 seed virus infection. For this, MDCK cells were infected at an MOI of 10 and assessed for virus titers by hemagglutination assay (HA) and infectious virions by 50% tissue culture infective dose ($TCID_{50}$) assay at 12 hpi. Intracellular vRNAs and vRNAs of released virions were quantified by real-time RT-qPCR. Fractions of infectious virus particles and quantities of vRNA per virion were calculated based on the virus particle concentrations that were derived from HA titers. For PR8-RKI virus, we obtained a vRNA copy number per virus particle of roughly 5 for S5, S7 and S8, which is in the same order of magnitude and thus, in reasonable agreement with an expected value of 1. Hence, numbers of vRNAs per virion of PR8-RKI virus were used for normalization for all remaining viruses (as a reference). S5, S7 and S8 were quantified representatively for all genome segments.

We did not find remarkable differences in the properties of OP7 seed viruses compared to PR8-RKI, PR8-NIBSC and the PP viruses. All viruses showed high infectious titers, most likely due to the predominant presence of fully infectious STV, which allowed us to infect cells at high MOI. However, upon infection with OP7 seed virus at an MOI of 10, we observed again an over-proportional quantity of intracellular S7 vRNA in relation to S5 and S8, similar to our previous single cell experiments. Interestingly, the levels of S5 and S8 were significantly reduced compared to PR8-RKI and PP virus replication (by at least one order of magnitude). Moreover, the majority of virus progeny from OP7 seed virus-infected cells were non-infectious. More specifically, the fraction of infectious virions ranged from 0.02% for OP7-5 to 0.7% for OP7-4. In comparison to PR8-RKI or PP virus replication, this corresponds to a reduction in the infectivity of produced virions of almost three $\log_{10}$ for OP7-4, and more than one $\log_{10}$ for OP7-5 seed virus infection. Also note that the HA titer upon OP7 seed virus infection was (on average) reduced by 0.8 $\log_{10}$ units compared to PR8-RKI, and at least 0.3 $\log_{10}$ units lower in comparison to PP virus replication. The low percentage of infectious virions cannot be explained by the presence of conventional DIPs (cDIPs), as the results of segment-specific RT-PCR did not indicate a pronounced accumulation of subgenomic RNAs in the produced virions upon OP7 seed virus infection. In the following, we refer to virus particles released in infections with OP7 seed viruses as "OP7 virions".

The low infectivity of OP7 virions can be rather explained by their low vRNA content. More specifically, the calculated number of S5 and S8 per virion was reduced by approximately one order of magnitude compared PR8-RKI and PP virus particles. Intriguingly, the number of S7 vRNA was not affected. Hence, this result clearly indicates that OP7 virions are incomplete with respect to their vRNA content (except for S7), which would render them unable to reproduce upon a single-hit infection. The remaining infectivity is most likely conferred by the presence of STV. Furthermore, OP7 virions appeared to be slightly smaller in comparison to PR8-RKI and PP virions, as indicated by negative stain transmission electron microscopy (ns-TEM). Yet, particle morphology did not seem to be affected, as we observed spherical OP7 virus particles with well-resolved surface spike proteins (similar to PR8-RKI and PP virions). In summary, we show that OP7 virions are non-infectious as a result of their lack in genomic vRNA content, with the exception of S7, which was predominantly incorporated.

Mutated vRNA of S7-OP7, Affecting Encoded Proteins, Packaging Signals and Promotor Regions Next, we determined the sequence of vRNAs from OP7 virions to elucidate whether they contain genomic mutations. For sequencing of the terminal ends, we improved a method which is based on circular ligation of RNA (de Wit et al., 2007, Rapid sequencing of the non-coding regions of influenza A virus. J Virol Methods 139, 85-89). Due to the limited volume of samples, only four OP7 and three PP viruses were sequenced. Our experiments revealed a significant amount of mutations on the vRNA of S7-OP7. The number of substitutions ranged from 36-41 in comparison to PR8-RKI, PP virus and the reference sequence (RefSeq) of PR8 (NC_002016.1) from the National Center for Biotechnology Information (NCBI). Note that the highest sequence similarities for S7-OP7 were found for PR8 sequences in the NCBI database. In contrast, S5 and S8 showed fewer alterations, with differences in 8-16 nucleotides (nt) compared to PR8-RKI virus and the NCBI RefSeq (NC_002019.1 for S5, and NC_002020.1 for S8) and 0-3 nt in comparison to PP virus.

FIG. 3 illustrates the 37 point mutations of S7-OP7 vRNA in relation to the RefSeq of Seq. ID No. 1, which concern several functional regions of the genome segment.

Of all mutations identified on S7-OP7 in relation to the different S7 sequences, we constrained them to 35 substitutions, which may potentially produce the unusual phenotype. The OP7 viruses showed an identical S7 sequence, except for OP7-4 that showed an additional substitution, which was excluded from analysis as the OP7 phenotype of this isolate was overall less pronounced. Furthermore, we did not consider substitutions to the RefSeq, as we did not compare its phenotype to OP7 virus in this study. Thus, in relation to the S7 sequences of PR8-RKI and all PP viruses, we observe 35 identical nucleotide-to-nucleotide substitutions.

These 35 substitutions of S7-OP7 of Seq. ID No. 2 concern several functional regions of the genome segment (FIG. 1). The coding region contains 32 (33) mutations, resulting in 10 conservative and two non-conservative amino acid (aa) substitutions for the encoded M1, and four and two mutations for M2, respectively. Note that substitution A/T27V is depicted for M2, as PR8-RKI virus contained an alanine (A) and PP viruses a tyrosine (T) at the 27th position. The M1 nuclear localization signal (NLS) and nuclear export signal (NES) did not show alterations, and no additional stop codons were observed in the M1 and M2 reading frames. Moreover, we did not find substitutions at sites that affect splicing of M2 mRNA, i.e. the donor, branch and acceptor site as well as the polypyrimidine tract.

Interestingly, three (four) mutations were observed in the untranslated regions (UTRs), which involve the promotor and segment-specific non-coding regions at both vRNA ends. The promotor regions are highly conserved and comprise the non-coding 13 and 12 nucleotides (nt) at the 5' and 3' end of vRNA, respectively. Yet, on S7-OP7 vRNA, we identified the G3A/C8U mutation, which was previously referred to as the "superpromotor" (Belicha-Villanueva et al., 2012, Recombinant influenza A viruses with enhanced levels of PB1 and PA viral protein expression. J Virol 86, 5926-5930). Further, we identified a substitution at the fourth position (C4U) at the 3' end, which is usually polymorphic (U/C), depending on the genome segment. Substitutions at these three positions were neither found on other segments of OP7 virions, nor on all segments of PP and PR8-RKI virus. Furthermore, the segment-specific genome packaging signal sequences of S7, which include the UTRs and proximal parts of the coding region at both vRNA ends, were affected by 16 (17) nucleotide substitutions. Taken together, the vRNA of S7-OP7 shows a significant amount of mutations, while the extent of substitutions in S5 and S8 sequences was lower. The 35 (37) substitutions were distributed in the entire genome segment, affecting the M1 and M2 protein sequence, promotor regions and genome packaging signals.

"Superpromotor" on S7-OP7 Causes Altered Viral RNA Synthesis Upon OP7 Seed Virus Infection Each genomic vRNA segment is encapsidated into a viral ribonucleoprotein (vRNP) complex, involving viral nucleoproteins (NP) and the tripartite viral polymerase. Once in the nucleus, they are engaged in both transcription of viral messenger RNA (mRNA) and replication of complementary RNA (cRNA). cRNAs are themselves encapsidated in cRNPs and serve as a replication intermediate for the synthesis of progeny vRNA. To study the potential effect of the promotor mutations (found on the vRNA of S7-OP7) on viral RNA synthesis upon OP7 seed virus infection, we next investigated intracellular viral RNAs by real-time RT-qPCR and viral proteins by western blot. In the following, we used PR8-RKI virus for reference/WT virus infection. Until 12 hpi, the vRNA of S7 in OP7 seed virus infection reached comparable quantities in comparison to S5, S7 and S8 of PR8-RKI virus replication. Yet, the level of S5 and S8 vRNA was significantly reduced (by approximately one order of magnitude), which is in agreement with our previous observation.

Interestingly, mRNA of S7 reached higher peak quantities compared to S5 and S8 and in relation to all mRNAs of PR8-RKI virus replication, with a three- to six-fold increase observed between 6-8 hpi. Similarly, S7 cRNA reached elevated levels upon OP7 seed virus infection in comparison to other segments' cRNA and compared to all measured cRNAs of PR8-RKI virus replication. This increase was roughly sevenfold between 6-8 hpi in relation to PR8-RKI virus replication. The quantity of S8 cRNA in OP7 seed virus infection was comparable to that of PR8-RKI virus replication; however, the level of S5 cRNA was slightly reduced. In addition, intracellular M1 protein appeared to accumulate to higher quantities upon OP7 seed virus infection in comparison to PR8-RKI virus replication, while the amount of nucleoprotein (NP) and polymerase acid (PA) proteins seemed to be reduced.

Previously, artificial IAVs carrying the G3A/C8U "superpromotor" on the vRNA of either S2 or S3 were reconstituted (Belicha-Villanueva et al., 2012, Recombinant influenza A viruses with enhanced levels of PB1 and PA viral protein expression. J Virol 86, 5926-5930). Upon infection, the observed phenotype showed identical features, regarding viral RNA and protein synthesis from the segments bearing the "superpromotor", as compared to S7 upon OP7 seed virus infection. Furthermore, the authors demonstrated a stronger type I interferon (IFN) induction as compared to viruses not having the "superpromotor". We obtained a similar finding, as indicated by an elevated IFN-beta and myxovirus resistant gene 1 (M×1) transcript level in cells infected with OP7 seed virus compared to cells infected with PR8-RKI virus, which does not contain the "superpromotor".

Enhanced Nuclear Accumulation of the Mutated M1-OP7 May Cause Nuclear Retainment of vRNPs Once in the nucleus, M1 mediates the nuclear export of vRNPs. As the M1 protein of OP7 virus (M1-OP7) showed modifications, we next explored whether intracellular protein trafficking was altered upon OP7 seed virus infection. To this end, we used imaging flow cytometry. Infected cells were stained using either anti-M1 or anti-vRNP monoclonal antibodies (mAbs) in combination with nuclear stains 7-AAD or DAPI, respectively. Fractions of respective proteins/complexes in the nucleus were calculated based on the amount of fluorescence signal that was co-localized with the nuclear signal.

Until 4.5 hpi, the fraction of M1 in the nucleus was steadily increasing in PR8-RKI virus replication, indicating the nuclear import subsequent to their production. Concurrently, from 3-4.5 hpi, the percentage of vRNPs in the nucleus shows a steep decrease which indicates nuclear export of the viral genomes. Hence, the accumulation of M1 in the nucleus coincided with the nuclear export of vRNPs. After 4.5 hpi, both fractions continuously decreased in the course of the viral replication cycle. In contrast, for OP7 seed virus-infected cells, we can observe a strong increase in the percentage of M1 in the nucleus even after 4.5 hpi. Images illustrate the enhanced nuclear accumulation of M1 upon OP7 seed virus infection compared to PR8-RKI virus replication at 9 hpi. In addition, while a large proportion of vRNPs appeared to leave the nucleus from 3-4.5 hpi, some vRNPs seemed to remain in the nucleus from 6 hpi onwards, as indicated in comparison to PR8-RKI virus replication. In summary, image flow cytometric analysis indicates an enhanced nuclear accumulation of the mutated M1-OP7 upon OP7 seed virus infection, which may cause the apparent nuclear retainment of a fraction of vRNPs.

OP7 Virus Interferes with Replication of IAVs in Co-Infection Studies

Conventional DI-RNAs (cDI-RNAs) are thought to have growth advantages over their FL counterparts, i.e. an enhanced genomic replication and a preferential incorporation into progeny virions. Intriguingly, the mutated vRNA of S7-OP7 seemed to have very similar advantages in propagation. We therefore hypothesized that OP7 virus may even share another feature with cDIPs: the interference with replication of STVs. To further explore this possibility, we simultaneously co-infected cells with IAV and OP7 virus.

Figure 2:
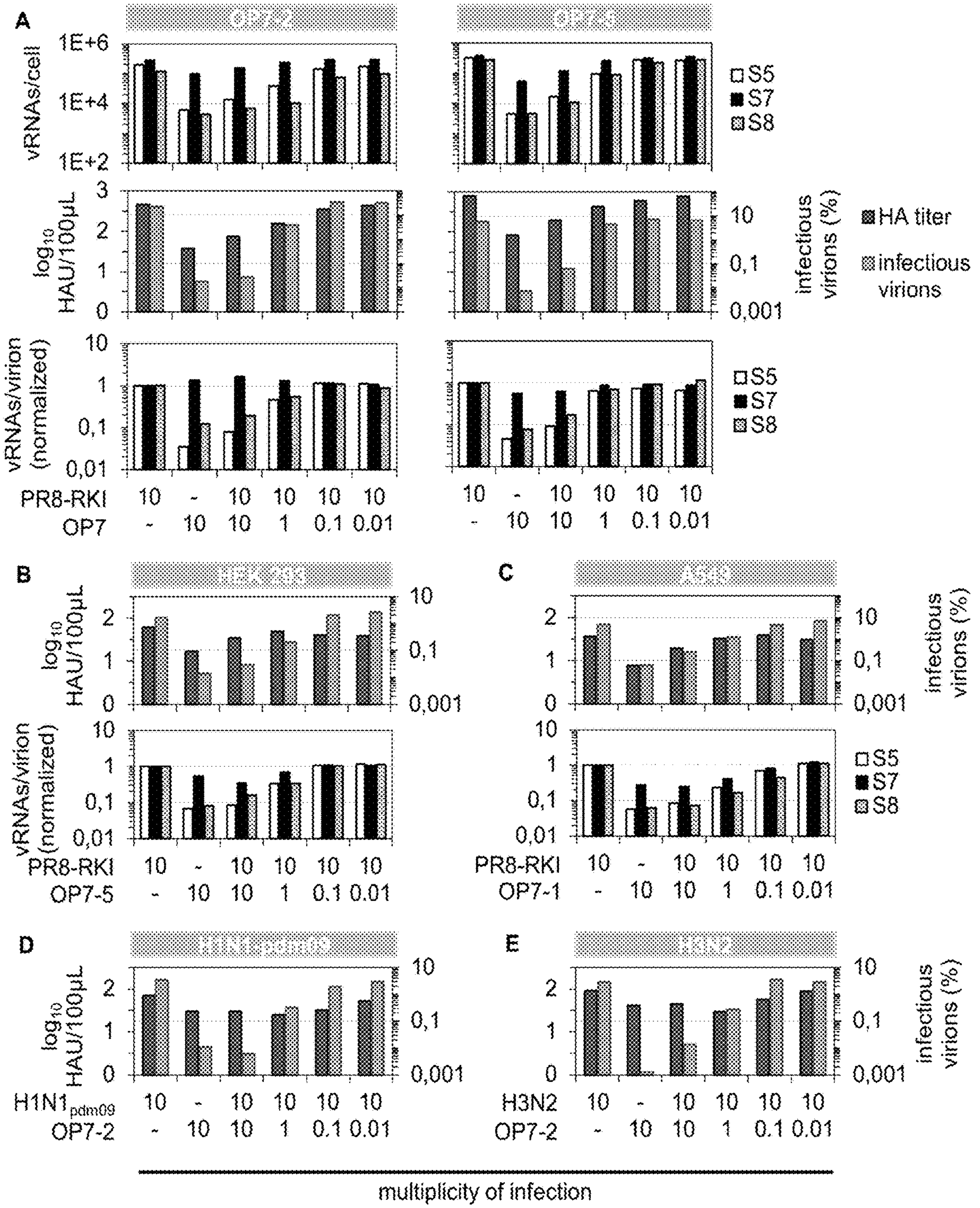
FIG. 2. Co-Infection of IAV-Infected Cells with OP7 Seed Virus Cells infected with wild type (WT) virus at an MOI of 10 were simultaneously co-infected with OP7 seed virus at the indicated MOIs. At 12 hpi (hours post infection), infectious virus titers were quantified by TCID50 assay, and intracellular and purified vRNAs from virions by real-time RT-qPCR. Data were used to calculate fractions of infectious virus and numbers of vRNAs per virion using the virus particle concentration derived from HA titer. Normalization of vRNAs per virion was based on PR8-RKI virus (as reference). Independent experiments were conducted, each using one OP7 seed virus. (A) Interference of different OP7 seed viruses with IAV replication in MDCK cells. (B and C) Co-infection of PR8-RKI-infected human HEK 293 (B) and A549 (C) cell lines with OP7 seed virus. (D and E) Interference of OP7 virus with H1N1-pdm09 (D) and H3N2 (E) virus replication in MDCK cells. Results of one representative experiment are shown for (B, C, D and E).

Indeed, the co-infection experiments showed an attenuated replication of PR8-RKI virus (FIG. 2A). In comparison to cells infected with only PR8-RKI (M01=10), the co-infected cells (both OP7 and PR8-RKI virus at an MOI of 10) showed a reduced HA titer (by 0.8 units), a severe reduction in the infectivity of the released virions (≈3 orders of magnitude) and an over-proportional quantity of S7 vRNA in relation to S5 and S8 (intracellularly and in the released virus particles). Hence, the same (yet less pronounced) phenotype as compared to cells infected with only OP7 seed virus (M01=10) was observed in such mixed infections. Further, the strength of interference could be out-diluted with decreasing MOIs of OP7 seed virus.

To explore whether OP7 virus also shows interference with PR8-RKI virus replication in human cell lines, we next used human embryonic kidney 293 (HEK 293) and A549 cells (derived from human lung carcinoma) in co-infection studies. Again, experiments revealed interference, as indicated by the reduction in HA titer, a strong decrease in the infectivity of released virions and an over-proportional level of S7 vRNA in the produced virus particles compared to cells infected with only PR8-RKI (FIG. 2B, 2C). Similarly, co-infection studies in MDCK cells also demonstrated interference with the pandemic influenza virus A/California/7/2009 of H1N1 subtype (H1N1-pdm09) and even with the heterologous H3N2 subtype influenza virus A/Hong Kong/4801/2014, as indicated by a reduction in HA titer and the infectivity of released virions (FIG. 2D, 2E). Taken together, our experiments demonstrated a strong interference of OP7 virus with replication of PR8-RKI virus in both, MDCK cells and two human cell lines as well as interference with H1N1-pdm09 and H3N2 virus replication.

Discussion

So far, DIPs were mainly identified and characterized regarding their internal genomic deletions. By contrast, in the present study, we report the discovery of a novel type of IAV-derived DIPs that contains nucleotide substitutions in one of its genome segments. OP7 virus shares very similar features with cDIPs upon co-infection with STV, i.e. (i) an enhanced genomic replication of the DI genome over other segments, (ii) its predominant packaging into progeny virions, (iii) an enhanced induction of innate immunity, (iv) released virus particles which are non-infectious due to the lack of genomic information, and (v) interference with replication of STV.

High-MOI single-cell infection studies allowed us to recognize the unusual OP7 phenotype in a subpopulation of individual infected cells, and to harvest the released OP7 virions in the supernatant of these cells. Multiplication of viruses in this supernatant was performed using approximately $1\times10^6$ cells, which can only result in a low MOI infection, as virus titers of single IAV-infected cells reach only up to (theoretically) roughly 1000 PFU. Typically, infections with virus seeds containing cDIPs under low MOI conditions can lead to high infectious virus titers, which was also true for the resulting OP7 seed viruses. These infection conditions reduce co-infection events and cells are mostly infected by single virus particles. Hence, STV-infected cells produce predominantly infectious viral progeny; however, initially, DIP-only infected cells cannot contribute to virus production. Yet, for a certain time window, these cells may still become co-infected with newly produced STV, which, in turn, converts these cells to a (primarily) DIP-producing form. Hence, for low MOI infections, infectious virions usually dominate in the released virus population. In contrast, using the resultant OP7 seed viruses at high MOIs, we observed very low fractions of released infectious virions; an outcome, which is also to be expected from seed viruses containing cDIPs as well. This infection condition fosters co-infections events and, thus, the complementation of DIP-infected cells with STVs early on. Hence, as a result of the propagation advantage of the DI genomes, mainly non-infectious DIPs accumulate in the resulting virus population.

Our data show that these released OP7 virions are non-infectious due to their reduced vRNA content. More specifically, compared to WT virions, the number of vRNA is reduced by roughly one order of magnitude, while the quantity of S7 was not affected. These calculated numbers can, theoretically, result in virus populations, where (i) only ≈10% of the particles are complete, i.e. they contain each of the eight different genome segments, while the remaining virions contain only S7 or (ii) all virus particles contain S7; yet, they lack a significant part of the remaining seven segments. However, as the fraction of infectious virions was reduced by more than two orders of magnitude (compared to WT virions), only the second scenario seems to be conclusive. The remaining infectivity can be explained by the presence of residual STV, the random packaging of eight functional segments (see below for more details), or the complementation of infected cells with all functional genome segments through co-infection. Furthermore, our conclusion, that OP7 virions are defective in virus replication is further supported by the results of plaque purification from PR8-NIBSC virus (which contains OP7 virus). It can be assumed that each plaque originates from the infection of a cell by a single virus particle. However, none of the resultant 43 virus isolates showed the OP7 virus phenotype in infection experiments, which indicates that OP7 virions are propagation-incompetent.

The segment-specific genome packaging signal sequences of S7 were affected by 16 (17) mutations, which may explain the unusual vRNA content of OP7 virions. Typically, virus assembly and budding is a well-organized process, in which eight different vRNAs are selectively incorporated into each virus particle, with the packaging signals being involved. However, depending on the strain, up to 20% of virions can still fail to package at least one vRNA. Furthermore, it was suggested that S7 plays a key role in the IAV genome packaging process, as already four mutations in the signal sequence can disrupt vRNA packaging (Hutchinson et al., 2008, Mutational analysis of cis-acting RNA signals in segment 7 of influenza A virus. J Virol 82, 11869-11879). Similar to our results of infection experiments using OP7 seed viruses, the authors observed a dramatic decrease in the percentage of released infectious virions (compared to WT virus replication) of more than two orders of magnitude. This decrease equaled the reduction predicted for a random packaging process, in which only a minority of virions would incorporate the complete genome. In contrast, Hutchinson and colleagues did not observe an over-representation of S7 vRNA in the released virus particles (Hutchinson et al., 2008, see above). It might be that the combination of a disrupted genome packaging and the observed over-proportional intracellular level of S7 vRNA can result in the formation of said virions. Alternatively, additional mechanisms may act on the mutated vRNA of S7-OP7. However, in the end, S7-OP7 predominates in OP7 virions over other genome segments; an observation that may show similarities to cDI-RNAs, which are preferentially packaged over their FL counterparts.

Previously, artificial IAVs carrying the G3A/C8U "super-promotor" on the vRNA of either S2 or S3 were reconstituted (Belicha-Villanueva et al., 2012, Recombinant influenza A viruses with enhanced levels of PB1 and PA viral protein expression. J Virol 86, 5926-5930). Upon infection, the observed phenotype showed very similar intracellular features, with respect to viral RNA and protein synthesis from the segments bearing G3A/C8U, as compared to S7-OP7 (which carries G3A/C8U) upon OP7 seed virus infection. More specifically, (i) a strong decrease in vRNA levels of all genome segments, except for the vRNA carrying G3A/C8U, (ii) an enhanced synthesis of mRNA, cRNA and protein derived from the said segment and (iii) increased levels of type I IFN in comparison to WT virus replication has been observed. Regarding the latter observation, it was shown that this increased induction was likely caused by elevated amounts of immunostimulatory RNA molecules. Such an enhanced induction of innate immunity is also observed for infections with conventional DIPs. The additional G4U substitution (described herein in S7-OP7) can also affect promotor function.

Importantly, the G3A/C8U mutation alone does not result in the whole OP7 virus phenotype, as vRNA segments bearing G3A/C8U were not predominantly packaged into progeny virions in the context of an infection (Belicha-Villanueva et al., 2012, Recombinant influenza A viruses with enhanced levels of PB1 and PA viral protein expression. J Virol 86, 5926-5930), unlike S7-OP7 in OP7 virus infection. This indicates that additional mutations (found on S7-OP7) are necessary, beyond G3A/C8U, for the defective and interfering phenotype of OP7 virus. Moreover, it was not described yet that the G3A/C8U mutation results in a DIP-like phenotype. The G3A/C8U substitutions were, so far, only artificially introduced into the vRNA of IAVs. It is, thus, remarkable that S7-OP7 seemed to have obtained G3A/C8U "naturally" by selection. As a result, the genomic vRNA of S7-OP7 accumulates to roughly ten-fold higher intracellular levels compared to other genome segments. This feature shows again similarities to conventional DI genomes, which are preferentially synthesized over their FL counterparts; yet, for another reason, i.e. presumably as a result of a faster accumulation, due to their reduced length The coding region of S7-OP7 showed 32 (33) mutations, resulting in both two non-conservative substitutions for the M1 and the M2 (ion channel) protein. Among other functions, both proteins are also important for virus assembly, which may provide an additional explanation for the irregular vRNA content of OP7 virions. Moreover, alterations in the proteins can also affect virus morphology, which shows a variety morphotypes, including filamentous virions.

The M1 protein is also involved in the nuclear export of vRNPs. Although we did not identify alterations in the NLS and NES of M1-OP7, the protein nevertheless showed an unusually high accumulation in the nucleus upon OP7 seed virus infection. Concurrently, compared to WT virus replication, it appeared that a fraction of vRNPs were retained in the nucleus. In this context, M1 is thought to mediate the binding of the viral nuclear export protein (NEP) and the vRNPs, which in turn forms a complex that is exported from the nucleus by the NES located of NEP. Hence, it is conceivable that the binding sites of M1-OP7 to NEP and/or the vRNPs are altered, which leads to their nuclear retainment. Note that a fraction of vRNPs are exported from the nucleus at early times post infection, which can be explained by the synthesis of some functional M1 from the co-infecting STV. The partial nuclear retainment of the genomic vRNPs may contribute to the reduced virus titer observed upon OP7 virus co-infection. Hence, it is conceivable that the perturbed function of the mutated M1-OP7 contributes to the interfering ability of OP7 virus, or even to its defect in virus replication.

OP7 virions may be a promising candidate for antiviral therapy as they show strong interference with virus replication of relevant homologous and heterologous IAV strains, and interference in human cell lines. Furthermore, the enhanced induction of innate immunity, observed upon OP7 seed virus infection, may be further beneficial in the context of antiviral therapy.

In summary, we propose that OP7 virions are a yet unrecognized form of DIPs, derived from IAVs. The vRNA of S7-OP7 exerts a strong inhibitory effect on IAV replication, reducing the production of viral components, while favoring its own reproduction and spread. In particular, the "superpromotor" confers the vRNA an advantage in genomic replication, while other unknown mechanisms, which might result from the mutated packaging signal, result in a predominant incorporation of the molecule into virus particles. Concurrently, the lack of other genomic vRNA segments in OP7 virus particles renders them defective in virus replication. Finally, due to its strong interfering ability with IAV replication, OP7 virions may turn out to be a promising candidate for antiviral therapy.

Hence, the nucleic acid molecules according to the present invention, in particular, in the piRNA of SEQ ID No. 3 represents suitable means as anti-viral agents having an inhibitory and interfering effect on influenza virus replication. Hence, the nucleic acid sequences according to the present invention as well as the composition and virus-like particles and viral vectors according to the present invention represent suitable vaccines and pharmaceutical compositions which allow prophylactic and therapeutic treatment of virus infection. The presence of the piRNA can inhibit the spread of a natural infection with virus, like influenza A viruses. Further, due to the positive effects on the innate immune response, further promotion of the anti-viral effect is likely.

The invention claimed is:

1. An isolated nucleic acid molecule comprising
   a) SEQ ID No. 2 containing the following substitutions of C3T, G4A, G8A, A100G, G113A, G130A, G240A, A241G, C334T, C353T, C361T, C370A, T371G, T385C, A401T, G434A, C442T, A443G, C453T, A454G, A524G, T643G, G645T, A648G, A667G, G670A, A716G, C793T, G801T, A805G, G874T, A887T, C888T, G894A, G943A, compared to the wild type sequence of SEQ ID No. 1;
   b) a nucleotide sequence having greater than 98% identity within the sequence of SEQ ID No. 2;
   c) a nucleotide sequence that hybridizes with the nucleotide sequence of a) or b) under stringent conditions;
   d) a nucleotide sequence complementary to any of the sequences a), b) or c); or
   e) mRNA derived from any one of the sequences a), b), c) or d).

2. The isolated nucleic acid molecule according to claim 1 comprising
   a) SEQ ID No. 3; or
   b) a nucleic acid sequence having greater than 98% identity with the sequence of SEQ ID No. 3;
   c) a nucleotide sequence that hybridizes with the nucleotide sequence of a) or b) under stringent conditions;
   d) a nucleotide sequence complementary to any of the sequences a), b) or c); or
   e) mRNA derived from any one of the sequences a), b), c) or d).

3. The isolated nucleic acid molecule according to claim 1 wherein at least the substituents at C3T and G8A are present.

4. The isolated nucleic acid molecule as claimed in claim 1 being RNA.

5. A composition comprising an isolated nucleic acid molecule according to claim 1.

6. A vector or plasmid comprising a nucleic acid molecule according to claim 1.

7. A virus-like particle, a viral vector or a virus particle containing a nucleic acid molecule according to claim 1.

8. The virus-like particle or the viral vector according to claim 7 further comprising a HA or NA of an influenza virus being an influenza virus active in the past infection season and/or the present infection season.

9. A method of treating a subject for a viral infection comprising administering the subject the virus-like particle, the viral vector or the virus particle according to claim 7.

10. A host cell containing the nucleic acid vector or plasmid according to claim 6.

11. Pharmaceutical composition containing a nucleic acid molecule according to claim 1, or a plasmid, host cell, viral vector or virus-like particle containing the nucleic acid molecule.

12. A therapeutic or prophylactic vaccine comprising the pharmaceutical composition of claim 11.

13. A method of treating a viral infection is caused by a virulent influenza virus in a subject in need thereof by administering the subject the pharmaceutical composition of claim 11.

14. The pharmaceutical composition according to claim 11 adapted for administration to a subject selected from the group consisting of a human, a pig, a horse, a dog, a cat, and a bird.

15. The pharmaceutical composition according to claim 11 configured for mucosal administration.

16. The pharmaceutical composition according to claim 15 wherein said mucosal administration is intranasal administration.

17. A method for treating a subject or prophylactically vaccinating a subject for influenza A virus infection by administering the subject with the pharmaceutical composition of claim 11.

18. A vaccine for vaccination against viral infection comprising a nucleic acid according to claim 1, or a vector, plasmid, virus-like particle, viral vector, or virus particle containing the nucleic acid.

19. The vaccine according to claim 18 configured for vaccination against influenza A virus infection.

20. A method for delivering immune protection to an individual by providing the individual with the pharmaceutical composition according to claim 11.

21. A composition or kit comprising a nucleic acid molecule according to claim 1, or a virus-like particle, viral vector, virus particle, vector, plasmid, host cell, wild type viral vector, wild type virus particle containing the nucleic acid molecule in form of a pharmaceutical composition for use in treating or protecting against viral infection.

22. A virus-like particle, a viral vector, or a virus particle according to claim 7 wherein said virus-like particle, viral vector, or virus particle demonstrates after infection at least one of i) a reduction in the total number of virus particles produced, ii) a severe reduction in the fraction of infectious virus produced, iii) a normal intracellular reproduction of the piRNA while a reproduction of all remaining genome segments apart from the piRNA is reduced, iv) an increased transcription of mRNA from piRNA compared to other genome segments, v) an enhanced number of proteins, translated from mRNA derived from piRNA, vi) perturbed intracellular trafficking of said protein, thus, leading to a perturbed intracellular trafficking of the viral nucleoproteins, vii) a normal incorporation of piRNA into virus particles in comparison to all genome segments of the wild type virus while the incorporation of other genome segments is reduced, and viii) a stronger induction of the innate immune response expressed by interferon-β expression is observable.

23. The virus-like particle, the viral vector or the virus particle containing a nucleic acid molecule according to claim 7 wherein the virus-like particle or the viral vector is an influenza virus or is derived from an influenza virus.

24. The virus-like particle, the viral vector or the virus particle containing a nucleic acid molecule according to claim 23 wherein the influenza virus is influenza A virus.

25. The vaccine for vaccination against viral infection according to claim 18 wherein the nucleic acid is an RNA molecule.

* * * * *